United States Patent
Ritland

(10) Patent No.: US 8,690,922 B2
(45) Date of Patent: Apr. 8, 2014

(54) DYNAMIC FIXATION DEVICE AND METHOD OF USE

(76) Inventor: Stephen Ritland, Flagstaff, AZ (US)

( * ) Notice: Subject to any disclaimer, the term of this patent is extended or adjusted under 35 U.S.C. 154(b) by 624 days.

(21) Appl. No.: 12/714,738

(22) Filed: Mar. 1, 2010

(65) Prior Publication Data

US 2010/0160969 A1    Jun. 24, 2010

Related U.S. Application Data

(63) Continuation of application No. 10/435,330, filed on May 8, 2003, now Pat. No. 7,682,375.

(60) Provisional application No. 60/390,181, filed on Jun. 19, 2002, provisional application No. 60/417,722, filed on Oct. 9, 2002, provisional application No. 60/379,167, filed on May 8, 2002.

(51) Int. Cl.
A61B 17/70    (2006.01)

(52) U.S. Cl.
USPC .......................................... 606/255; 606/257

(58) Field of Classification Search
USPC ................................................ 606/250–263
See application file for complete search history.

(56) References Cited

U.S. PATENT DOCUMENTS

| | | |
|---|---|---|
| 2,191 A | 7/1841 | Pitney |
| 569,839 A | 10/1896 | Roeloffs |
| 605,652 A | 6/1898 | Pitt |
| 1,090,746 A | 3/1914 | Nourse |
| 1,097,978 A | 5/1914 | Johnson |
| 2,611,434 A | 9/1952 | Mugler |
| 3,467,079 A | 9/1969 | James |
| 3,470,872 A | 10/1969 | Grieshaber |
| 3,875,595 A | 4/1975 | Froning |
| 3,893,454 A | 7/1975 | Hagelin |
| 4,041,939 A | 8/1977 | Hall |
| 4,232,660 A | 11/1980 | Coles |
| 4,440,168 A | 4/1984 | Warren |
| 4,481,947 A | 11/1984 | Chester |
| 4,545,374 A | 10/1985 | Jacobson |

(Continued)

FOREIGN PATENT DOCUMENTS

| | | |
|---|---|---|
| CA | 2320821 | 8/1999 |
| DE | 9004960 | 8/1991 |

(Continued)

OTHER PUBLICATIONS

Caspar "Technique of Microsurgery: Microsurgery of the Lumbar Spine: Principles and Techniques in Spine Surgery"; Aspen Publications; 1990; 105-122.

(Continued)

*Primary Examiner* — Mary Hoffman
(74) *Attorney, Agent, or Firm* — Fox Rothschild LLP

(57) ABSTRACT

A dynamic fixation device is provided that allows the vertebrae to which it is attached to move in flexion within the normal physiological limits of motion, while also providing structural support that limits the amount of translation motion beyond normal physiological limits. The present invention includes a flexible portion and two ends that are adapted for connection to pedicle screws. In at least one embodiment of the present invention, the normal axis of rotation of the vertebrae is substantially duplicated by the dynamic fixation device. The flexible portion of the dynamic fixation device can include a geometric shape and/or a hinge portion.

9 Claims, 17 Drawing Sheets

(56) References Cited

U.S. PATENT DOCUMENTS

| | | |
|---|---|---|
| 4,573,448 A | 3/1986 | Kambin |
| 4,617,922 A | 10/1986 | Griggs |
| 4,620,460 A | 11/1986 | Gonzales, Jr. |
| 4,686,972 A | 8/1987 | Kurland |
| 4,736,738 A | 4/1988 | Lipovsek et al. |
| 4,743,260 A | 5/1988 | Burton |
| 4,747,394 A | 5/1988 | Watanabe |
| 4,798,111 A | 1/1989 | Cheeseman |
| 4,803,976 A | 2/1989 | Frigg et al. |
| 4,817,587 A | 4/1989 | Janese |
| 4,862,891 A | 9/1989 | Smith |
| 4,863,423 A | 9/1989 | Wallace |
| 4,882,958 A | 11/1989 | McNeeley |
| 4,889,112 A | 12/1989 | Schachner et al. |
| 4,946,458 A | 8/1990 | Harms et al. |
| 4,995,875 A | 2/1991 | Coes |
| 5,002,542 A | 3/1991 | Frigg |
| 5,002,576 A | 3/1991 | Fuhrmann et al. |
| 5,018,507 A | 5/1991 | Montaldi |
| 5,024,213 A | 6/1991 | Asher et al. |
| 5,026,373 A | 6/1991 | Ray et al. |
| 5,030,220 A | 7/1991 | Howland |
| 5,030,223 A | 7/1991 | Anderson et al. |
| 5,035,232 A | 7/1991 | Lutze et al. |
| 5,048,379 A | 9/1991 | Gramera |
| 5,052,373 A | 10/1991 | Michelson |
| 5,055,104 A | 10/1991 | Ray |
| 5,084,043 A | 1/1992 | Hertzmann |
| 5,098,435 A | 3/1992 | Stednitz |
| 5,106,376 A | 4/1992 | Mononen |
| 5,129,899 A | 7/1992 | Small et al. |
| 5,129,900 A | 7/1992 | Asher et al. |
| 5,133,720 A | 7/1992 | Greenberg |
| 5,135,525 A | 8/1992 | Biscoping |
| 5,148,724 A | 9/1992 | Rexford |
| 5,158,543 A | 10/1992 | Lazarus |
| 5,165,306 A | 11/1992 | Hellon |
| 5,180,393 A | 1/1993 | Commarmond |
| 5,195,541 A | 3/1993 | Obenchain |
| 5,217,007 A | 6/1993 | Ciaglia |
| 5,246,016 A | 9/1993 | Lieber et al. |
| 5,275,600 A | 1/1994 | Allard et al. |
| 5,275,611 A | 1/1994 | Behl |
| 5,279,567 A | 1/1994 | Ciaglia |
| 5,282,863 A | 2/1994 | Burton |
| 5,292,309 A | 3/1994 | Van Tassel |
| 5,303,694 A | 4/1994 | Mikhail |
| 5,304,179 A | 4/1994 | Wagner |
| 5,306,275 A | 4/1994 | Bryan |
| 5,306,309 A | 4/1994 | Wagner et al. |
| 5,312,360 A | 5/1994 | Behl |
| 5,312,405 A | 5/1994 | Korotko et al. |
| 5,330,473 A | 7/1994 | Howland |
| 5,330,474 A | 7/1994 | Lin |
| 5,330,476 A | 7/1994 | Hiot et al. |
| 5,356,413 A | 10/1994 | Martins et al. |
| 5,363,841 A | 11/1994 | Coker |
| 5,363,853 A | 11/1994 | Lieber et al. |
| 5,387,213 A | 2/1995 | Breard et al. |
| 5,415,661 A * | 5/1995 | Holmes .................... 606/255 |
| 5,423,816 A | 6/1995 | Lin |
| 5,431,639 A | 7/1995 | Shaw |
| 5,431,651 A | 7/1995 | Goble |
| D361,381 S | 8/1995 | Koros et al. |
| 5,439,464 A | 8/1995 | Shapiro |
| 5,466,238 A | 11/1995 | Lin |
| 5,472,426 A | 12/1995 | Bonati |
| 5,474,555 A | 12/1995 | Puno et al. |
| 5,480,401 A | 1/1996 | Navas |
| 5,484,440 A | 1/1996 | Allard |
| 5,484,445 A | 1/1996 | Knuth |
| 5,489,274 A | 2/1996 | Chu |
| 5,489,308 A | 2/1996 | Kuslich et al. |
| 5,498,262 A | 3/1996 | Bryan |
| 5,499,983 A | 3/1996 | Hughes |
| 5,501,684 A | 3/1996 | Schlapfer et al. |
| 5,512,038 A | 4/1996 | O'Neal et al. |
| 5,545,166 A | 8/1996 | Howland |
| 5,549,612 A | 8/1996 | Yapp et al. |
| 5,558,622 A | 9/1996 | Greenberg |
| 5,562,663 A | 10/1996 | Wisnewski et al. |
| 5,565,502 A | 10/1996 | Glimcher et al. |
| 5,569,300 A | 10/1996 | Redmon |
| 5,584,831 A | 12/1996 | McKay |
| 5,584,833 A | 12/1996 | Fournet-Fayard et al. |
| 5,591,166 A | 1/1997 | Bernhardt et al. |
| 5,591,235 A | 1/1997 | Kuslich |
| 5,593,409 A | 1/1997 | Michelson |
| 5,601,550 A | 2/1997 | Esser |
| 5,603,714 A | 2/1997 | Kaneda et al. |
| 5,611,778 A | 3/1997 | Brinon |
| 5,613,968 A | 3/1997 | Lin |
| 5,628,740 A | 5/1997 | Mullane |
| 5,630,816 A | 5/1997 | Kambin |
| 5,643,263 A | 7/1997 | Simonson |
| 5,643,264 A | 7/1997 | Sherman et al. |
| 5,645,544 A | 7/1997 | Tai et al. |
| 5,645,599 A | 7/1997 | Samani |
| 5,649,925 A | 7/1997 | Barbera Alacreu |
| 5,662,620 A | 9/1997 | Lieber et al. |
| 5,667,506 A | 9/1997 | Sutterlin |
| 5,672,175 A | 9/1997 | Martin |
| 5,673,463 A | 10/1997 | Godefroy et al. |
| 5,682,392 A | 10/1997 | Richelsoph et al. |
| 5,683,389 A | 11/1997 | Orsak |
| 5,687,739 A | 11/1997 | McPherson |
| 5,690,632 A | 11/1997 | Schwartz et al. |
| 5,691,397 A | 11/1997 | Glimcher et al. |
| 5,695,993 A | 12/1997 | Fukudome et al. |
| 5,702,455 A | 12/1997 | Saggar |
| 5,716,355 A | 2/1998 | Jackson et al. |
| 5,716,415 A | 2/1998 | Steffee |
| 5,725,528 A | 3/1998 | Errico et al. |
| 5,735,850 A | 4/1998 | Baumgartner et al. |
| 5,735,851 A | 4/1998 | Errico et al. |
| 5,735,899 A | 4/1998 | Schwartz et al. |
| 5,743,853 A | 4/1998 | Lauderdale |
| 5,746,720 A | 5/1998 | Stouder, Jr. |
| 5,746,741 A | 5/1998 | Kraus et al. |
| 5,752,957 A | 5/1998 | Ralph et al. |
| 5,766,221 A | 6/1998 | Benderev et al. |
| 5,766,253 A | 6/1998 | Brosnahan, III |
| 5,772,582 A | 6/1998 | Huttner et al. |
| 5,782,832 A | 7/1998 | Larsen et al. |
| 5,785,648 A | 7/1998 | Min |
| 5,785,710 A | 7/1998 | Michelson |
| 5,785,712 A | 7/1998 | Runciman et al. |
| 5,792,044 A | 8/1998 | Foley |
| 5,797,912 A | 8/1998 | Runciman et al. |
| 5,800,435 A | 9/1998 | Errico et al. |
| 5,810,816 A | 9/1998 | Roussouly et al. |
| 5,810,817 A | 9/1998 | Roussouly et al. |
| D399,955 S | 10/1998 | Koros et al. |
| 5,819,257 A | 10/1998 | Chin |
| 5,827,328 A | 10/1998 | Buttermann |
| 5,833,645 A | 11/1998 | Lieber et al. |
| 5,836,948 A | 11/1998 | Zucherman et al. |
| RE36,020 E | 12/1998 | Moore et al. |
| 5,851,207 A | 12/1998 | Cesarone |
| 5,860,977 A | 1/1999 | Zucherman et al. |
| 5,865,847 A | 2/1999 | Kohrs et al. |
| 5,865,848 A | 2/1999 | Baker |
| 5,876,404 A | 3/1999 | Zucherman et al. |
| 5,882,344 A | 3/1999 | Stouder, Jr. |
| 5,885,285 A | 3/1999 | Simonson |
| 5,885,299 A | 3/1999 | Winslow et al. |
| 5,885,300 A | 3/1999 | Tokuhashi et al. |
| 5,891,147 A | 4/1999 | Moskovitz et al. |
| 5,895,352 A | 4/1999 | Kleiner |
| 5,895,390 A | 4/1999 | Moran et al. |
| 5,897,593 A | 4/1999 | Kohrs et al. |

(56) References Cited

U.S. PATENT DOCUMENTS

| | | |
|---|---|---|
| 5,899,901 A | 5/1999 | Middleton |
| 5,902,231 A | 5/1999 | Foley |
| 5,902,304 A | 5/1999 | Walker et al. |
| 5,904,650 A | 5/1999 | Wells |
| 5,906,616 A | 5/1999 | Pavlov et al. |
| 5,913,818 A | 6/1999 | Co et al. |
| 5,928,139 A | 7/1999 | Koros |
| 5,928,233 A | 7/1999 | Apfelbaum et al. |
| 5,931,838 A | 8/1999 | Vito |
| 5,938,663 A | 8/1999 | Petreto |
| 5,944,658 A | 8/1999 | Koros et al. |
| 5,947,965 A | 9/1999 | Bryan |
| 5,954,635 A | 9/1999 | Foley |
| 5,954,671 A | 9/1999 | O'Neil |
| 5,961,516 A | 10/1999 | Graf |
| 5,967,970 A | 10/1999 | Cowan |
| 5,968,098 A | 10/1999 | Winslow |
| 5,971,920 A | 10/1999 | Nagel |
| 5,976,135 A | 11/1999 | Sherman et al. |
| 5,976,146 A | 11/1999 | Ogawa |
| 5,984,924 A | 11/1999 | Asher et al. |
| 5,984,925 A * | 11/1999 | Apgar ............... 606/284 |
| 5,996,447 A | 12/1999 | Bayouth |
| 5,997,539 A | 12/1999 | Errico et al. |
| 6,004,322 A | 12/1999 | Berstein |
| 6,007,487 A | 12/1999 | Foley et al. |
| 6,010,520 A | 1/2000 | Pattison |
| 6,017,342 A | 1/2000 | Rinner |
| 6,027,533 A | 2/2000 | Olerud |
| 6,045,579 A | 4/2000 | Hochsheuler et al. |
| 6,048,342 A | 4/2000 | Zucherman et al. |
| 6,050,997 A | 4/2000 | Mullane |
| 6,063,088 A | 5/2000 | Winslow |
| 6,068,630 A | 5/2000 | Zucherman et al. |
| 6,074,390 A | 6/2000 | Zucherman et al. |
| 6,074,393 A | 6/2000 | Sitoto |
| 6,080,155 A | 6/2000 | Michelson |
| 6,080,193 A | 6/2000 | Hochshuler et al. |
| 6,081,741 A | 6/2000 | Hollis |
| 6,083,225 A | 7/2000 | Winslow et al. |
| 6,083,226 A | 7/2000 | Fiz |
| 6,090,112 A | 7/2000 | Zucherman et al. |
| 6,102,948 A | 8/2000 | Brosnahan, III |
| 6,113,602 A | 9/2000 | Sand |
| 6,117,137 A | 9/2000 | Halm et al. |
| 6,117,174 A | 9/2000 | Nolan |
| 6,120,434 A | 9/2000 | Kimura |
| 6,120,506 A | 9/2000 | Kohrs et al. |
| 6,123,705 A | 9/2000 | Michelson |
| 6,123,706 A | 9/2000 | Lange |
| 6,132,430 A | 10/2000 | Wagner |
| D433,296 S | 11/2000 | Yamakawa |
| 6,146,383 A | 11/2000 | Studer et al. |
| 6,149,652 A | 11/2000 | Zucherman et al. |
| 6,149,686 A | 11/2000 | Kulish et al. |
| 6,150,825 A | 11/2000 | Prokopp et al. |
| 6,152,871 A | 11/2000 | Foley |
| 6,152,926 A | 11/2000 | Zucherman et al. |
| 6,156,006 A | 12/2000 | Brosens |
| 6,156,038 A | 12/2000 | Zucherman et al. |
| 6,159,179 A | 12/2000 | Simonson |
| 6,162,170 A | 12/2000 | Foley |
| 6,162,236 A | 12/2000 | Osada |
| D436,513 S | 1/2001 | Yamakawa |
| 6,176,823 B1 | 1/2001 | Foley |
| 6,176,861 B1 | 1/2001 | Bernstein et al. |
| 6,179,838 B1 | 1/2001 | Fiz |
| D438,074 S | 2/2001 | Marr |
| 6,183,471 B1 | 2/2001 | Zucherman et al. |
| 6,187,005 B1 | 2/2001 | Brace et al. |
| 6,190,387 B1 | 2/2001 | Zucherman et al. |
| 6,190,414 B1 | 2/2001 | Young et al. |
| 6,196,696 B1 | 3/2001 | Shiao |
| 6,196,969 B1 | 3/2001 | Bester et al. |
| 6,197,002 B1 | 3/2001 | Peterson |
| 6,206,822 B1 | 3/2001 | Foley |
| 6,206,826 B1 | 3/2001 | Mathews et al. |
| 6,206,882 B1 * | 3/2001 | Cohen ............... 606/283 |
| 6,206,885 B1 | 3/2001 | Ghahremani et al. |
| 6,206,922 B1 | 3/2001 | Zdeblick et al. |
| 6,206,923 B1 | 3/2001 | Boyd et al. |
| 6,210,413 B1 | 4/2001 | Justis et al. |
| 6,214,004 B1 | 4/2001 | Coker |
| 6,217,509 B1 | 4/2001 | Foley |
| 6,224,597 B1 | 5/2001 | Coker |
| 6,224,608 B1 | 5/2001 | Ciccolella |
| 6,224,631 B1 | 5/2001 | Kohrs |
| 6,231,575 B1 | 5/2001 | Krag |
| 6,235,030 B1 | 5/2001 | Zucherman et al. |
| 6,238,397 B1 | 5/2001 | Zucherman et al. |
| 6,245,072 B1 | 6/2001 | Zdeblick et al. |
| 6,248,104 B1 | 6/2001 | Chopin et al. |
| 6,248,106 B1 | 6/2001 | Ferree |
| 6,258,097 B1 | 7/2001 | Cook |
| 6,261,287 B1 | 7/2001 | Metz-Stavenhagen |
| 6,264,658 B1 | 7/2001 | Lee et al. |
| 6,267,763 B1 | 7/2001 | Castro |
| 6,267,764 B1 * | 7/2001 | Elberg ............... 606/255 |
| 6,267,765 B1 | 7/2001 | Taylor et al. |
| 6,270,498 B1 | 8/2001 | Michelson |
| 6,273,914 B1 | 8/2001 | Papas |
| 6,273,917 B1 | 8/2001 | Inoue |
| 6,279,501 B1 | 8/2001 | Taylor, Jr. |
| 6,283,966 B1 | 9/2001 | Houfburg |
| 6,287,309 B1 | 9/2001 | Baccelli et al. |
| 6,287,313 B1 | 9/2001 | Sasso |
| 6,287,343 B1 | 9/2001 | Kuslich et al. |
| 6,290,700 B1 | 9/2001 | Schmotzer |
| 6,293,949 B1 * | 9/2001 | Justis et al. ............... 606/279 |
| 6,296,609 B1 | 10/2001 | Brau |
| 6,299,614 B1 | 10/2001 | Kretschmer et al. |
| 6,302,842 B1 | 10/2001 | Auerbach et al. |
| 6,309,390 B1 | 10/2001 | Le Courdic et al. |
| 6,309,391 B1 | 10/2001 | Crandall et al. |
| 6,312,432 B1 | 11/2001 | Leppelmeier |
| 6,332,883 B1 | 12/2001 | Zucherman et al. |
| 6,342,057 B1 | 1/2002 | Brace |
| 6,348,058 B1 | 2/2002 | Melkent et al. |
| 6,354,176 B1 | 3/2002 | Nordlin |
| 6,355,038 B1 | 3/2002 | Pisharodi |
| 6,361,541 B1 | 3/2002 | Barnhart |
| D455,766 S | 4/2002 | Marty |
| 6,364,881 B1 * | 4/2002 | Apgar et al. ............... 606/284 |
| 6,368,320 B1 | 4/2002 | Le Couedic et al. |
| 6,368,350 B1 | 4/2002 | Erickson et al. |
| 6,368,351 B1 | 4/2002 | Glenn et al. |
| 6,371,959 B1 | 4/2002 | Trice |
| 6,371,968 B1 | 4/2002 | Kogasaka |
| 6,379,354 B1 | 4/2002 | Rogozinski |
| 6,391,058 B1 | 5/2002 | Kuslich et al. |
| 6,395,033 B1 | 5/2002 | Pepper |
| 6,418,821 B1 | 7/2002 | Yamakawa |
| 6,425,901 B1 | 7/2002 | Zhu et al. |
| 6,428,472 B1 | 8/2002 | Haas |
| 6,440,169 B1 * | 8/2002 | Elberg et al. ............... 623/17.16 |
| 6,440,170 B1 | 8/2002 | Jackson |
| 6,443,953 B1 | 9/2002 | Perra et al. |
| 6,443,989 B1 | 9/2002 | Jackson |
| 6,461,330 B1 | 10/2002 | Miyagi |
| 6,461,359 B1 | 10/2002 | Tribus et al. |
| 6,471,724 B2 | 10/2002 | Zdeblick et al. |
| 6,475,219 B1 * | 11/2002 | Shelokov ............... 606/281 |
| 6,478,798 B1 | 11/2002 | Howland |
| 6,506,151 B2 | 1/2003 | Estes et al. |
| 6,520,907 B1 | 2/2003 | Foley |
| 6,524,238 B2 | 2/2003 | Velikaris et al. |
| 6,530,880 B2 | 3/2003 | Pagliuca |
| 6,530,926 B1 | 3/2003 | Davidson |
| 6,540,756 B1 | 4/2003 | Vaughan |
| 6,551,320 B2 | 4/2003 | Lieberman |
| 6,554,831 B1 | 4/2003 | Rivard et al. |
| 6,562,046 B2 | 5/2003 | Sasso |
| 6,562,073 B2 | 5/2003 | Foley |
| 6,565,569 B1 | 5/2003 | Assaker et al. |

(56) References Cited

U.S. PATENT DOCUMENTS

| | | |
|---|---|---|
| 6,569,164 B1 | 5/2003 | Assaker et al. |
| 6,576,017 B2 | 6/2003 | Foley et al. |
| 6,579,292 B2 | 6/2003 | Taylor |
| 6,585,738 B1 | 7/2003 | Mangione et al. |
| 6,585,769 B1 | 7/2003 | Muhanna et al. |
| 6,595,993 B2 | 7/2003 | Donno et al. |
| 6,599,290 B2 | 7/2003 | Bailey et al. |
| 6,610,062 B2 | 8/2003 | Bailey et al. |
| 6,626,904 B1 | 9/2003 | Jammet et al. |
| 6,626,906 B1 | 9/2003 | Young |
| 6,648,887 B2 | 11/2003 | Ashman |
| 6,652,527 B2 | 11/2003 | Zucherman et al. |
| 6,671,725 B1 | 12/2003 | Noel, Jr. et al. |
| 6,676,661 B1 | 1/2004 | Benllock et al. |
| 6,679,833 B2 | 1/2004 | Smith et al. |
| 6,682,532 B2 | 1/2004 | Johnson et al. |
| 6,685,705 B1 | 2/2004 | Taylor |
| 6,692,434 B2 | 2/2004 | Ritland |
| 6,736,816 B2 | 5/2004 | Ritland |
| 6,743,257 B2 | 6/2004 | Castro |
| 6,749,613 B1 | 6/2004 | Conchy et al. |
| 6,749,614 B2 | 6/2004 | Teitelbaum et al. |
| 6,752,832 B2 | 6/2004 | Neumann |
| 6,761,719 B2 | 7/2004 | Justis et al. |
| 6,783,528 B2 | 8/2004 | Vincent-Prestigiacomo |
| 6,851,430 B2 | 2/2005 | Tsou |
| 6,875,211 B2 | 4/2005 | Nichols et al. |
| 6,916,319 B2 | 7/2005 | Munting |
| 6,916,330 B2 | 7/2005 | Simonson |
| 6,929,606 B2 | 8/2005 | Ritland |
| 6,951,538 B2 | 10/2005 | Ritland |
| 6,955,678 B2 | 10/2005 | Gabriel et al. |
| 6,966,910 B2 | 11/2005 | Ritland |
| 6,974,480 B2 | 12/2005 | Messerit et al. |
| 6,991,632 B2 | 1/2006 | Ritland |
| 7,008,421 B2 | 3/2006 | Daniel et al. |
| 7,115,142 B2 | 10/2006 | Muhanna et al. |
| 7,166,073 B2 | 1/2007 | Ritland |
| 7,207,992 B2 | 4/2007 | Ritland |
| 7,344,539 B2 | 3/2008 | Serhan et al. |
| 7,632,292 B2 | 12/2009 | Sengupta et al. |
| 7,753,937 B2 | 7/2010 | Chervitz et al. |
| 7,758,582 B2 | 7/2010 | Ferrante et al. |
| 7,828,825 B2 | 11/2010 | Bruneau et al. |
| 7,951,170 B2 | 5/2011 | Jackson |
| 2001/0005796 A1 | 6/2001 | Zdeblick et al. |
| 2001/0010021 A1 | 7/2001 | Boyd et al. |
| 2001/0012942 A1 | 8/2001 | Estes |
| 2001/0027320 A1 | 10/2001 | Sasso |
| 2001/0034521 A1 | 10/2001 | Bailey et al. |
| 2001/0047207 A1 | 11/2001 | Michelson |
| 2002/0011135 A1 | 1/2002 | Hall |
| 2002/0013586 A1 | 1/2002 | Justis |
| 2002/0016592 A1 | 2/2002 | Branch |
| 2002/0022764 A1 | 2/2002 | Smith |
| 2002/0029082 A1 | 3/2002 | Muhanna |
| 2002/0049368 A1 | 4/2002 | Ritland |
| 2002/0052603 A1 | 5/2002 | Nichols et al. |
| 2002/0058948 A1 | 5/2002 | Arlettza |
| 2002/0068973 A1 | 6/2002 | Jackson |
| 2002/0068975 A1 | 6/2002 | Teitelbaum et al. |
| 2002/0077632 A1 | 6/2002 | Tsou |
| 2002/0082695 A1 | 6/2002 | Neumann |
| 2002/0107571 A1 | 8/2002 | Foley |
| 2002/0107572 A1 | 8/2002 | Foley et al. |
| 2002/0111625 A1 | 8/2002 | Richelsoph et al. |
| 2002/0120270 A1 | 8/2002 | Trieu et al. |
| 2002/0123668 A1 | 9/2002 | Ritland |
| 2002/0143235 A1 | 10/2002 | Pagliuca |
| 2003/0045874 A1 | 3/2003 | Thomas |
| 2003/0083688 A1 | 5/2003 | Simonson |
| 2003/0083689 A1 | 5/2003 | Simonson |
| 2003/0093078 A1 | 5/2003 | Ritland |
| 2003/0109880 A1 | 6/2003 | Shirado et al. |
| 2003/0139812 A1 | 7/2003 | Garcia et al. |
| 2003/0144665 A1 | 7/2003 | Munting |
| 2003/0171470 A1* | 9/2003 | Kurz et al. .................... 524/284 |
| 2003/0171749 A1* | 9/2003 | Le Couedic et al. ............ 606/61 |
| 2003/0171751 A1 | 9/2003 | Ritland |
| 2003/0187431 A1 | 10/2003 | Simonson |
| 2003/0195087 A1 | 10/2003 | Moore et al. |
| 2003/0220689 A1 | 11/2003 | Ritland |
| 2003/0236447 A1 | 12/2003 | Ritland |
| 2004/0002708 A1 | 1/2004 | Ritland |
| 2004/0073215 A1* | 4/2004 | Carli ............................... 606/61 |
| 2004/0106997 A1 | 6/2004 | Lieberson |
| 2004/0138534 A1 | 7/2004 | Ritland |
| 2004/0172023 A1 | 9/2004 | Ritland |
| 2004/0181223 A1 | 9/2004 | Ritland |
| 2004/0254428 A1 | 12/2004 | Ritland |
| 2005/0004593 A1 | 1/2005 | Simonson |
| 2005/0020920 A1 | 1/2005 | Ritland |
| 2005/0027360 A1 | 2/2005 | Webb et al. |
| 2005/0049587 A1 | 3/2005 | Jackson |
| 2005/0119656 A1 | 6/2005 | Ferrante et al. |
| 2005/0143737 A1 | 6/2005 | Paffard et al. |
| 2005/0149023 A1 | 7/2005 | Ritland |
| 2005/0149191 A1 | 7/2005 | Cragg et al. |
| 2005/0192579 A1 | 9/2005 | Jackson |
| 2005/0203517 A1 | 9/2005 | Jahng et al. |
| 2005/0203519 A1 | 9/2005 | Harms et al. |
| 2005/0209594 A1 | 9/2005 | Loeb |
| 2005/0228233 A1 | 10/2005 | Ritland |
| 2006/0009768 A1 | 1/2006 | Ritland |
| 2006/0025770 A1 | 2/2006 | Schlapfer et al. |
| 2006/0041259 A1 | 2/2006 | Paul et al. |
| 2006/0064090 A1 | 3/2006 | Park |
| 2006/0069390 A1 | 3/2006 | Frigg et al. |
| 2006/0079899 A1 | 4/2006 | Ritland |
| 2006/0085076 A1 | 4/2006 | Krishna et al. |
| 2006/0195087 A1 | 8/2006 | Sacher et al. |
| 2006/0205525 A1 | 9/2006 | Owen |
| 2006/0255074 A1 | 11/2006 | Amir |
| 2006/0265074 A1 | 11/2006 | Krishna et al. |
| 2006/0276794 A1 | 12/2006 | Stern |
| 2007/0016193 A1 | 1/2007 | Ritland |
| 2007/0233090 A1 | 10/2007 | Naifeh et al. |
| 2008/0071275 A1 | 3/2008 | Ferree |

FOREIGN PATENT DOCUMENTS

| | | |
|---|---|---|
| EP | 0820731 | 1/1998 |
| EP | 1585427 | 11/2003 |
| EP | 1658815 | 5/2006 |
| FR | 2735351 | 12/1996 |
| FR | 2755844 | 5/1998 |
| FR | 2796828 | 2/2001 |
| FR | 2799949 | 4/2001 |
| FR | 2812185 | 2/2002 |
| JP | H07-008504 | 1/1998 |
| JP | H11-501235 | 2/1999 |
| JP | H11-502742 | 3/1999 |
| JP | 2000-33091 | 2/2000 |
| WO | 95/08298 | 3/1995 |
| WO | 96/29947 | 10/1996 |
| WO | 97/06742 | 2/1997 |
| WO | 97/32533 | 9/1997 |
| WO | 99/09902 | 3/1999 |
| WO | 99/40866 | 8/1999 |
| WO | 00/18306 | 4/2000 |
| WO | 00/57801 | 10/2000 |
| WO | 01/64144 | 9/2001 |
| WO | 01/67973 | 9/2001 |
| WO | 02/007621 | 1/2002 |
| WO | 02/36026 | 1/2002 |
| WO | 02/060330 | 8/2002 |
| WO | 02/002022 | 10/2002 |
| WO | 02/102259 | 12/2002 |
| WO | 03/026523 | 4/2003 |
| WO | 03/073908 | 9/2003 |
| WO | 03/094699 | 11/2003 |
| WO | 2003/105704 | 12/2003 |

(56) References Cited

FOREIGN PATENT DOCUMENTS

| WO | 2004/052218 | 6/2004 |
|---|---|---|
| WO | 2004/075778 | 9/2004 |
| WO | 2004/089244 | 10/2004 |

OTHER PUBLICATIONS

China Chemical Reporter, "Rapid Development of Polyether Ether Ketone", CNCIC Chemdata Inc 2004, 2 pages.
Green, "Body Building—Medical Materials for Systems and Scaffolding," Materials World, Journal of the Institute of Materials, vol 10, No. 2, 2001, 4 pages.
Green, "Effects of Gamma Sterilisation on Implant Grade Polyetheretherketone," Invibio Inc, Lancashire, United Kingdom, undated, 1 page.
Green, "In Vivo Biostability Study on Polyaryletheretherketone Biomaterial," Invibio Inc Lancashire, United Kingdom, undated, 2 pages.
Green, et al. "A Polyaryletherketone Biomaterial for Use in Medical Implant Applications," Lancashire, United Kingdom, 2001, 1 page.
Green, et al. "Polyetheretherketone Polymer and Compounds for Surgical Applications," Lancashire, United Kingdom, undated, 9 pages.
Green, Stuart, "PEEK-Optima Polymer in the Implantable Medical Device Industry," Invibio Inc Lancashire, United Kingdom, undated, 2 pages.
Hilton et al.; "Meditronic Sofamor Danek METRX Microdiscectomy Surgical Technique Brochure"; 2000.
Invibio, Biomaterials Solutions, "High Performance PEEK-Optima Biocompatible Polymer Chosen for Dental Abutment Healing Caps," Invibio Inc Lancashire, United Kingdom, undated, 1 page.
Invibio, Biomaterials Solutions, "High Performance PEEK-Optima Biocompatible Polymer Chosen for New Generation Heart Valve," Invibio Inc., Lancashire, United Kingdom, undated, 1 page.
Invibio, Biomaterials Solutions, "Peek~Classix," Invibio Inc., Lancashire, United Kingdom, 2003, 2 pages.
Invibio, Biomaterials Solutions, "PEEK-Optima Polymer: Performance Purity Flexibility Endurance," Invibio Inc., Lancashire, United Kingdom, 2004, 3 pages.
Invibio, Biomaterials Solutions, "PEEK-Optima, Composite Hip," Invibio Inc., Lancashire, United Kingdom, undated, 2 pages.
Invibio, Biomaterials Solutions, "PEEK-Optima, Spiked Washers," Invibio Inc., Lancashire, United Kingdom, undated, 1 page.
Kambin; "Arthroscopic Microdiscectomy: Minimal Intervention in Spinal Surgery"; National Ubrary of Medicine; 1991; 67-100.
Kambin; "Percutaneous Posterolateral Discectomy"; Clincial Orthopaedics and Related Research. Section II; 145-154119.
Savitz; Same-Day Microsurgical Arthroscopic Latera-Approach Laser-Assisted (SMALL) Fluoroscopic Discectomy; Journal of Neurosurgery; Jun. 1994; 1039-1045.
Schaffer et al.; "Percutaneous Posterolateral Lumbar Discectomy and Decompression with a 6.9 Millimeter Cannula"; Journal of Bone and Joint Surgery; 1991; 822-831.
Sofamor Danek Video Systems Brochure.
"New Minimally Invasive Techniques, Improve Outcome of Spine Surgeries", Medtronic Sofamor Danek.
Tangram Technology Ltd., "Polymer Data File: Polyether Ether Ketone-PEEK," Available at http://www.tangram.co.uk/TI-Polymer-PEEK.html, 2001, 5 pages.
Web pages, http://brainlab.com, Apr. 2, 2002; 5 pages.
Wiltse; "New Uses and Refinements of the Paraspinal Approach to the Lumbar Spine"; Spine; 1988; 13(6):696-706.
Office Action dated Mar. 7, 2011 in U.S. Appl. No. 11/425,987.
Office Action dated Jan. 27, 2011 in Australian Application No. 2006262057.
Office Action dated Sep. 6, 2011 in U.S. Appl. No. 11/223,530.
Final Office Action dated Mar. 22, 2012 in U.S. Appl. No. 11/223,530.
Office Action dated Aug. 28, 2012, in Canadian Application No. 2612943.
European Extended Search Report dated Apr. 27, 2012 in EPO Application No. 12001018.6.
European Extended Search Report dated Apr. 27, 2012 in EPO Application No. 12001019.4.
Notice of Allowance dated Jun. 14, 2010 in Canadian Application No. 2484923.
Final Office Action Dated Nov. 28, 2011 in U.S. Appl. No. 11/425,987.
Office Action dated Nov. 25, 2011 in Japanese Application No. 2008-518436 (English translation included).
Final Office Action dated Dec. 11, 2012 in Japanese Application No. 2008-518436 (English translation included).
Re-Issue U.S. Appl. No. 10/165,991, filed on Jun. 10, 2002 by Simonson.
Office Action dated Oct. 24, 2008, issued in Australian Application No. 2008201824.
Notice of Allowance dated Sep. 14, 2010, issued in Australian Application No. 2008201824.
Office Action dated Jul. 9, 2010, issued in U.S. Appl. No. 11/425,987.
Office Action dated Feb. 25, 2013 in U.S. Appl. No. 12/729,956.
Office Action dated Feb. 22, 2013 in U.S. Appl. No. 12/729,422.
EPO Office Action dated Feb. 22, 2013 in EPO Application No. 12001019.4.
Appeal Brief filed Apr. 23, 2013 in U.S. Appl. No. 11/223,530.
Office Action dated Nov. 14, 2013 in U.S. Appl. No. 11/223,530.
EPO Office Action dated Jan. 21, 2013, issued in European Application No. 12001018.6.
U.S. Appl. No. 10/165,991 to Simonson, filed on Jun. 10, 2002.
Supplemental Search Report dated Jun. 10, 2008, issued in EPO Application No. 04758814.0.
Office Action dated Aug. 29, 2008, issued in EPO Application No. 04758814.0.
International Search Report dated Feb. 11, 2005, issued in Application No. PCT/US2004/010277.
Written Opinion dated Feb. 11, 2005, issued in Application No. PCT/US2004/010277.
International Preliminary Report dated Oct. 27, 2005, issued in Application No. PCT/US2004/010277.
Written Opinion dated Oct. 14, 2005, issued in Application No. PCT/US2003/014615.
International Preliminary Examination Report dated Jan. 10, 2006, issued in Application No. PCT/US2003/014615.
International Preliminary Report dated Jan. 10, 2008, issued in Application No. PCT/US2006/024491.
International Search Report dated Sep. 25, 2007, issued in Application No. PCT/US2006/024491.
Written Opinion dated Sep. 25, 2007, issued in Application No. PCT/US2006/024491.
Notification of Reasons for Refusal, dated Oct. 17, 2006, issued in South Korean Application No. 10/2005/7018906.
Notification of Decision to Grant, dated May 30, 2007, issued in South Korean Application No. 10/2005/7018906.
Office Action dated Dec. 16, 2008, issued in Japanese Application No. 2006-509659.
Office Action dated Feb. 28, 2007, issued in Canada Application No. 2520741.
Office Action dated Jan. 19, 2007, issued in Chinese Application No. 200480014833.8.
Office Action dated Dec. 5, 2008, issued in Chinese Application No. 200480014833.8.
Office Action dated Jun. 15, 2010, issued in European Application No. 03726737.4.
Examiner's First Report dated Mar. 27, 2007, issued in Australian Application No. 2004228019.
Examiner's First Report dated Oct. 17, 2007, issued in Australian Application No. 2003228960.
Office Action dated Aug. 11, 2009, issued in U.S. Appl. No. 11/223,530.
Final Office Action dated Apr. 13, 2010, issued in U.S. Appl. No. 11/223,530.
Office Action dated Aug. 24, 2007, issued in U.S. Appl. No. 10/435,330.

(56) References Cited

OTHER PUBLICATIONS

Office Action dated Jan. 11, 2005, issued in U.S. Appl. No. 10/435,330.
Office Action dated May 5, 2005, issued in U.S. Appl. No. 10/435,330.
Office Action dated Aug. 28, 2006, issued in U.S. Appl. No. 10/435,330.
Office Action dated Mar. 26, 2007, issued in U.S. Appl. No. 10/435,330.
Office Action dated Apr. 16, 2008, issued in U.S. Appl. No. 10/435,330.
Office Action dated Oct. 28, 2008, issued in U.S. Appl. No. 10/435,330.
Final Office Action dated Jul. 23, 2009, issued in U.S. Appl. No. 10/435,330.
Notice of Allowance dated Nov. 23, 2009, issued in U.S. Appl. No. 10/435,330.
Office Action dated Aug. 17, 2004, issued in U.S. Appl. No. 10/406,895.
Office Action dated Dec. 13, 2004, issued in U.S. Appl. No. 10/406,895.
Notice of Allowance dated Jun. 1, 2005, issued in U.S. Appl. No. 10/406,895.
Supplemental Notice of Allowance dated Oct. 13, 2005, issued in U.S. Appl. No. 10/406,895.
Office Action dated May 7, 2009, issued in Japanese Application No. 2004-502799.
Final Office Action dated Feb. 10, 2010, issued in Japanese Application No. 2004-502799.
Supplemental Search Report dated Mar. 24, 2010, issued in European Application No. 03726737.4.
Office Action dated Jun. 19, 2009, issued in Chinese Application No. 200680030105.5.
Office Action dated Sep. 14, 2009, issued in Canadian Application No. 2484923.

* cited by examiner

DYNAMIC FIXATION DEVICE AND METHOD OF USE

CROSS-REFERENCE TO RELATED APPLICATIONS

The present application is a continuation application of U.S. patent application Ser. No. 10/435,330 filed on May 8, 2003, which claimed the benefit of: U.S. Provisional Patent Application No. 60/379,167 filed May 8, 2002 entitled "Dynamic Fusion System"; U.S. Provisional Patent Application No. 60/390,181 filed Jun. 19, 2002 entitled "Dynamic Fusion System"; and U.S. Provisional Patent Application No. 60/417,722 filed Oct. 9, 2002 entitled "Dynamic Fusion System," all of which are incorporated herein by reference in their entireties. Cross-reference and incorporation thereof is also made to U.S. Nonprovisional patent application Ser. No. 10/406,895 filed on Apr. 4, 2003 entitled "Dynamic Fixation Device And Method of Use," now U.S. Pat. No. 6,966,910.

FIELD OF THE INVENTION

This invention relates generally to securement devices and, more particularly, to a flexible rod or device along a portion thereof that is capable of flexibly securing vertebrae together.

BACKGROUND OF THE INVENTION

The lumbar spine absorbs a remarkable amount of stress and motion during normal activity. For the majority of the population, the healing response of the body is able to stay ahead of the cumulative effects of injury, wear, and aging, and yet still maintain stability with reasonable function. In some cases, however, the trauma or stress exceeds the ability of the body to heal, leading to local breakdown and excessive wear, and frequently also leads to local instability. Accordingly, degenerative change with age superimposed on baseline anatomy in the lumbar spine leads to problems including instability, pain and neurologic compromise in some patients. In some cases, the local anatomy may not provide the same protection to the motion segment, thereby aggravating this breakdown. Although rehabilitation, conditioning, the limitation of stress, and time to recover are effective treatments for most patients, there is a significant failure rate with persistent pain, disability and potential neurologic deficit.

Referring now to FIGS. 1, and 2, two side views of a pair of adjacent vertebral bodies are shown. FIG. 1 illustrates two vertebra $V_1$ and $V_2$ of the spine in a neutral position. As shown in FIG. 2, when a person leans forwards, the spine undergoes flexion. The anterior portion of the spine comprises a set of generally cylindrically shaped bones which are stacked one on top of the other. These portions of the vertebrae are referred to as the vertebral bodies $VB_1$ and $VB_2$, and are each separated from the other by the intervertebral discs D. The pedicles $P_1$ and $P_2$ comprise bone bridges which couple the anterior vertebral body VB to the posterior portion of each vertebra. At each intervertebral joint or disc D, flexion involves a combination of anterior sagittal rotation and a small amplitude anterior translation.

The intervertebral joint is a complex structure comprising an intervertebral disc anteriorly, and paired zygapophyseal joints posteriorly. The disc functions as an elastic support and connection between the vertebra, and allows for flexion and extension of the spine, as well as limited rotation and translation. The zygapophyseal joints and associated anatomy allow for significant flexion and extension while providing constraints in translation and rotation.

The primary bending motion in the lumbar spine is flexion and extension in an anterior/posterior plane. This occurs in the range approximating 10-15 degrees of flexion and extension. In a young or normal lumbar spine, this motion occurs about an axis in the mid to posterior portion of the disc. This is associated with a distraction or subluxation of the facet joints or posterior elements of 10-15 mm. This occurs not about a pure axis, but about a neutral zone, or a centroid of rotation associated with the lumbar disc. The normal elasticity of the disc, joints and ligaments, and the degree of play or freedom associated with these joints, as well as the nature of the loads applied to the spine contribute to the size of this region of rotation. In some cases, the recurrent loads and motion on the disc and associated trauma to disc and motion segment exceed the natural rate of healing or repair of the body. In this situation, there is breakdown in the motion segment associated with loss of the normal axis of rotation. As increasing subluxation occurs with segmental motion, there is a dramatic shift in the axis of rotation with displacement occurring within the disc space or frequently to some point outside of the disc. Therefore, in the situation of a failing motion segment, there is breakdown in the centroid of rotation with associated translation of the vertebral segments. This translation is allowed by both breakdown occurring in the disc and instability associated with both wear and degeneration of the zygapophyseal joints. The underlying anatomy of the motion segment and joints allows for significantly greater stress on the disc and contributes to degeneration both in the disc and joints.

Traditionally, surgical treatment has been directed at treating neural compromise, or if the pain, instability, or risk of instability is considered sufficient, a segmental fusion has been considered. More recently, stabilization procedures have been tried over the past several years including artificial discs and ligaments and elastomeric constructs to protect the spine. Arthroplasty techniques to maximize function and reduce the dynamic effects on adjacent segments are a more recent approach with less follow-up as to long-term results. A challenge in designing such a system is constraining motion in a normal physiologic range.

Spinal fusion surgery is a method of fusing at least two mobile segments of the spine to knit them together as one unit and eliminate motion between the segments. Current spinal fixation systems offer several drawbacks. Rigid fusion constructs do not allow relative movement between the vertebrae that are fused using a construct comprising a pedicle screw, connector mechanism, and rigid rod. Furthermore, rigid implants are known to create significant amounts of stress on the components of the construct, including the pedicle screws and the rod, as well as the bone structure itself. These stresses may even cause the rigid rod to break. In addition, the stresses transferred to the pedicle screws may cause the screws to loosen or even dislodge from the vertebrae, thereby causing additional bone damage.

Artificial discs may replace a failing disc and approximate a normal centroid or axis of rotation; however, placement of such a device is technically demanding and replaces the normal disc with a mechanical replacement with uncertain long-term results. The artificial disc will be subject to wear without the healing potential of the body to heal itself.

It is also desirable with some patients to have a spinal implant system that allows the vertebral column to settle naturally under the weight of the human body. Human bone heals more readily under some pressure. In a rigid spinal implant system, the patient's spinal column may be unnaturally held apart by the structure of the implant. It is possible that this stretching of the vertebrae, in relation to one another, results in delayed or incomplete healing of the bone.

Posterior devices placed with pedicle fixation may provide some stabilization, however, the natural motion of such devices does not necessarily act to mimic normal physiology. In a healthy lumbar spine the axis of rotation or neutral area for motion is situated near the inferior posterior third of the lumbar disc. A desirable artificial system would closely approximate physiologic motion. However, to date, posterior systems have failed to address these concerns.

Several existing patents disclose fusion devices. For example, U.S. Pat. No. 5,415,661 discloses a device that includes a curvilinear rod such that the implant supposedly restores normal biomechanical function to the vertebrae of the spine receiving the implant. However, the '661 patent does not disclose a device having structure other than a curvilinear shape that has a radius of curvature of between 0 to 180 degrees. In addition, the '661 patent does not disclose the concept of providing an anteriorly projected pivot point that models the natural articulation of the subject vertebrae by using a structure that provides a virtual rotation zone substantially identical to the rotation zone provided by the patient's vertebrae. In addition, as seen in FIG. 3 of the '661 patent, the device disclosed in the '661 patent utilizes a body 4 having a central section 10 having an anteriorly oriented position relative to its ends 6a, 6b.

U.S. Pat. No. 6,293,949 also discloses a spinal stabilization device intended for use along the cervical vertebrae, and intended to be installed along the anterior side of the vertebrae.

U.S. Pat. No. 6,440,169 discloses a device that attaches to the spinous processes of two vertebrae and has a leaf spring that allows the device to compress and then recover spontaneously after the stress has ceased. However, the '169 patent does not address a construct that includes an anteriorly projected pivot point that allows the vertebrae to articulate when the spine undergoes flexion.

In view of the above, there is a long felt but unsolved need for a method and system that avoids the above-mentioned deficiencies of the prior art and that provides an effective system that is relatively simple to employ and requires minimal displacement or removal of bodily tissue.

SUMMARY OF THE INVENTION

The present invention provides a device that can be implanted and that provides for a specified amount of forward bending motion, thereby allowing anterior sagittal rotation between the vertebrae that receive the implant. Reference is hereby made for the incorporation of the conventional descriptive terms of motion and other content presented in *Clinical Anatomy of the Lumbar Spine and Sacrum* by Nikolai Bogduk, third edition, published by Churchill Livingstone, 1999. Although anterior sagittal rotation or flexion between vertebrae is normal, significant anterior sagittal translation or sliding motion between vertebrae is not. Thus, by allowing some amount of rotational motion while protecting against translation, the patient's condition or injury can be protected, thus promoting the healing process, while subsequently providing some ability to rotate one vertebra relative to an adjacent vertebra, thereby allowing for improved spinal motion following surgery and recovery. Accordingly, as described herein, various implants, including a number of rod configurations having flexible portions are presented that provide a device having the ability to elongate and bend. Thus, it is a first aspect of the present invention to provide a device that elongates, and a second aspect of the present invention to provide a device that bends. More particularly, the present invention is a dynamic fixation device that includes a flexible rod portion, wherein the flexible rod portion can include a geometric shape and/or a hinge portion. These dynamic fixation devices are constructed of a material of an appropriate size, geometry, and having mechanical properties such that they bend, thus allowing the vertebrae associated with the implant to rotate relative to one another, similar to the movement of a natural spine.

A dynamic fixation device is a quasi-flexible, semi-rigid fixation construct that allows some measure of motion between the vertebrae attached to the dynamic fixation device. Dynamic fixation of the lumbar spine provides means of protecting lumbar structures and allows for healing without proceeding to a lumbar arthrodesis. The constraints on such a system are in some ways different than for a rigid or near rigid construct, such as that used for fusion.

At the present time, pedicle fixation is an accepted method of fixing to the spine. In the situation of a lumbar fusion, a relatively rigid construct is appropriate to stabilize the spine and allow healing of the bony structures. In the situation of providing protection to the lumbar structures, a flexible system is appropriate to limit but not stop the motion of lumbar elements. The flexible elements in such a system need to accomplish several objectives. The primary objective is to allow physiologic motion of the spine, while protecting against excessive or non-physiologic movement. A secondary consideration is to protect the pedicle fixation from undue stress that could loosen the fixation at its bony interface.

The normal instantaneous axis of rotation of the lumbar spine occurs typically near the lower posterior third of the disc. Conventional pedicle fixation of the spine typically places the fixation rod or plate at the dorsal aspect of the apophyseal joint or posterior to the joint. Therefore, it is appropriate to consider a construct that effectively shifts this rotation point anteriorly toward the physiologic axis.

A group of geometries exist, which if applied to a posterior device, will constrain the subluxation of the segment and maintain the rotation in or close to the normal zone or axis of rotation. The indication for use is to constrain the stresses and motion within a range which will allow the body's normal healing response to maintain adequate competence in the motion segment to avoid development of instability or neurologic deficit and minimize pain or arthritis. The important features allow for maintenance of physiologic motion without the abnormal subluxation or translation that are associated with a degenerating disc and contribute to further degeneration. Thus, it is a separate aspect of the invention to provide a construct that limits excessive subluxation or translation.

Although the motion is complex related to the range of stresses which may be applied, it is nonetheless possible to provide a device so that while in compression, movement is axial or accompanied by slight dorsal translation, and that while in flexion allows both separation of posterior elements and slight ventral translation allowing rotation about the posterior portion of the disc.

Accordingly, it is an aspect of the present invention to provide a device that allows for some limited motion, thereby decreasing the stresses placed on the various component parts of the implant, as well as the affected vertebrae. It is a further aspect of the present invention to provide a device whose motion is designed to model the bending motion of the spine. Several separate embodiments of the present invention accomplish such tasks.

It is a separate aspect of the present invention to provide a construct that geometrically accommodates the human spinal anatomy, while providing a structural member that provides an anteriorly projected zone of rotation.

In a first embodiment, an implantable elastomeric material may be used, or a surgically implantable alloy can be used that includes a geometric shape having a plurality of arms (e.g., four arms) with an interior open region between the arms. In one example of this embodiment, the geometric shape is rectangular, such that the arms of the geometric shape are situated at 90 degree angles relative to each other. Upon deformation due to flexion of the spine, the geometric shape deforms, and the 90 degree angles between the arms change such that the geometric shape expands and becomes a parallelogram. In a separate aspect of the invention, the convergence segments of the arms include partially circular corners. Alternatively, the partially circular corners may be of a different shape, such as partially triangular. In a separate aspect of this embodiment, the inside surface of the interior sidewalls of the arms of the geometric shape have an interior surface that is at an angle of 90 degrees relative to a planar surface of the geometric shape. Attached to the exterior of the geometric shape near two opposing corners are two rod arms. The rod arms allow the device to be connected to connectors, which interconnect the device to pedicle screws. In a separate aspect of this embodiment, each rod arm may be situated at different angles and locations along the geometric shape, thereby influencing the location of the projected pivot point in the plane of the geometric shape upon flexion of the spine.

In yet a separate embodiment, a dynamic fixation device utilizes at least two adjacent geometric shapes that act in an accordion manner; however, this embodiment serves to project the effective pivot point anterior relative to the device. Therefore, the projected pivot point mimics the natural rotational axis of the vertebrae to which the device is attached. In a modification of this embodiment, more than two adjacent geometric shapes are combined to form the flexible portion of the device. One aspect of this embodiment and its modification is that smaller geometric shapes may be used with the addition of more geometric shapes. Consequently, a smaller profile dynamic fixation device can be provided, while at the same time having an effective pivot point that is projected anteriorly a sufficient distance to mimic the natural rotational axis of the vertebrae to which the device is attached.

In yet a separate embodiment, a dynamic fixation device is provided that includes a modified geometric shape that serves as the flexible portion of the device. The modified geometric shape incorporates an opening or void space that allows the device to elongate and deform to accommodate flexion of the spine.

In a yet a separate embodiment of the invention, the dynamic fusion device includes a geometric shape with an interior hollow region, preferably having sloped interior sidewalls. This feature allows the device to bend in a direction transverse to the plane of the geometric shape. The angle of the interior sidewalls can vary depending upon the desired amount of projection of the pivot point, which acts as a virtual axis of rotation for the device.

While the dynamic fixation devices described herein act to naturally control the axis or region of rotation within the device, it is also advantageous to consider the disc as part of the construct. If the disc is assumed to be competent as regards axial loads as opposed to translational loads, this competence can be used to control the disc height and concomitantly, the anterior portion of the implant and vertebral construct. Thus, in yet a separate embodiment, this allows a posterior construct having a rotatable anterior-posterior segment to effectively control translation within a specific range of motion of the segmental construct. Although there is a slight translation allowed, this is well within the natural region of rotation. This embodiment preferably includes a hinged portion having pin. If anterior-posterior segment or hinged arm is considered to be an elastomeric segment, its function depends on the translational forces being less than required to cause buckling of this segment. Controlling the shape of cross-section of this segment can allow forward bending of the spine while still maintaining competence in compression in the range of forces encountered in the implanted situation.

For the above described devices, first and second rod arms are attached to either end of the flexible construct, with the other end of the rod arms attached to connectors, which in turn are connected to pedicle screws that are inserted into vertebrae of the spine. During flexion and extension each vertebra exhibits an arcuate motion in relation to the vertebra below. The center of the arc lies below the moving vertebra. The dynamic fusion device provides a device for allowing movement of the vertebrae, with a forwardly or anteriorly projected pivot location that models and substantially aligns with the actual pivot point of rotation for the vertebrae to which the device is attached. Accordingly, the dynamic fusion device of the present invention provides a bendable rod for fusion that mimics the movement of the vertebrae of the spine.

The dynamic portions of the various embodiments of the present invention lengthen as they are elongated and shorten as they compressed. This characteristic allows the devices to be implanted in the spine with a pedicle screw system, and while the actual construct is positioned well dorsal in the spine, it allows the spine to function as though there were a flexible construct in the anterior column of the spine.

In use, a problematic spinal disc is initially identified by a physician. During surgery, an incision is made through the skin and muscle overlying the implant location of the spine. Then a first pedicle screw is inserted into a first vertebra and a second pedicle screw is inserted into a second vertebra. The surgeon then attaches the dynamic fixation device to the pedicle screws using either an adjustable connector or an end connector that is integrally formed as a part of the dynamic fixation device.

Various embodiments have been described in this summary of the invention but such embodiments are by no means to be deemed limiting to the "present invention" and the detailed description, the figures and the claims should be referred to in there totality to appreciate the true scope and breath of the present invention. Moreover, while much of the above discussion has focused on devices and particular configurations, various aspects of the present invention relate to surgical methods, methods of making such devices and methods of use which are also to be understood as being part of the present invention.

Additional advantages of the present invention will become readily apparent from the following discussion, particularly when taken together with the accompanying drawings.

BRIEF DESCRIPTION OF THE DRAWINGS

FIG. 6b is a front elevation view of the device shown in FIG. 6a;

FIG. 6c is a rear elevation view of the device shown in FIG. 6a;

FIG. 6d is a side elevation view of the device shown in FIG. 6a;

FIG. 10b is a side elevation view of a portion of the device shown in FIG. 10a;

The above listed drawings are not necessarily to scale.

DETAILED DESCRIPTION OF THE PREFERRED EMBODIMENT

While the present invention will be described more fully hereinafter with reference to the accompanying drawings in which particular embodiments and methods of implantation are shown, it is to be understood at the outset that persons skilled in the art may modify the invention herein described while achieving the functions and results of this invention. Accordingly, the descriptions which follow are to be understood as illustrative and exemplary of specific structures, aspects and features within the broad scope of the present invention and not as limiting of such broad scope.

As noted above, at each intervertebral joint or disc D, flexion involves a combination of anterior sagittal rotation and a small amplitude anterior translation. The various embodiments of the present invention allow for controlled rotation while limiting translation within an acceptable, normal physiological range.

Figure 1:
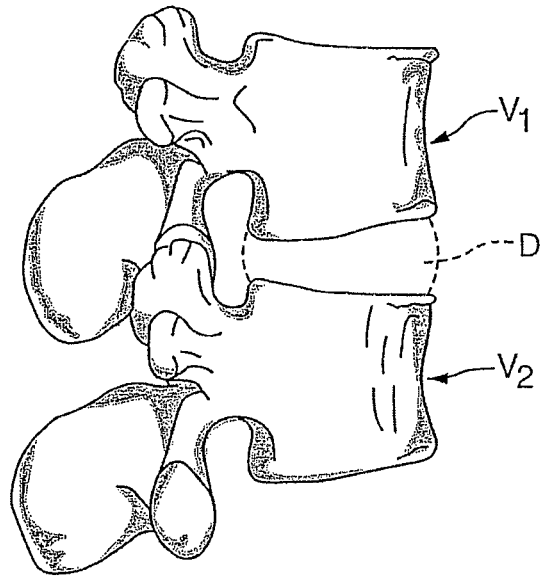
FIG. 1 is a side perspective view of two vertebra in a neutral position.
Figure 2:
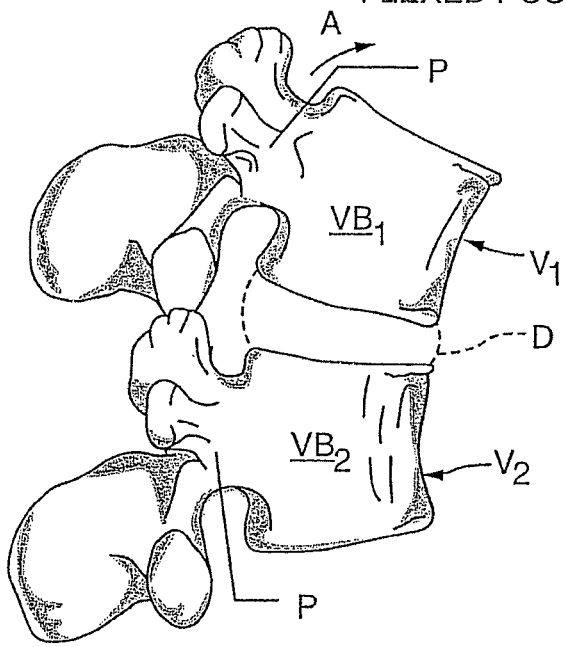
FIG. 2 is a side perspective view of the two vertebra shown in FIG. 1 in a condition of flexion.
Figure 3A:
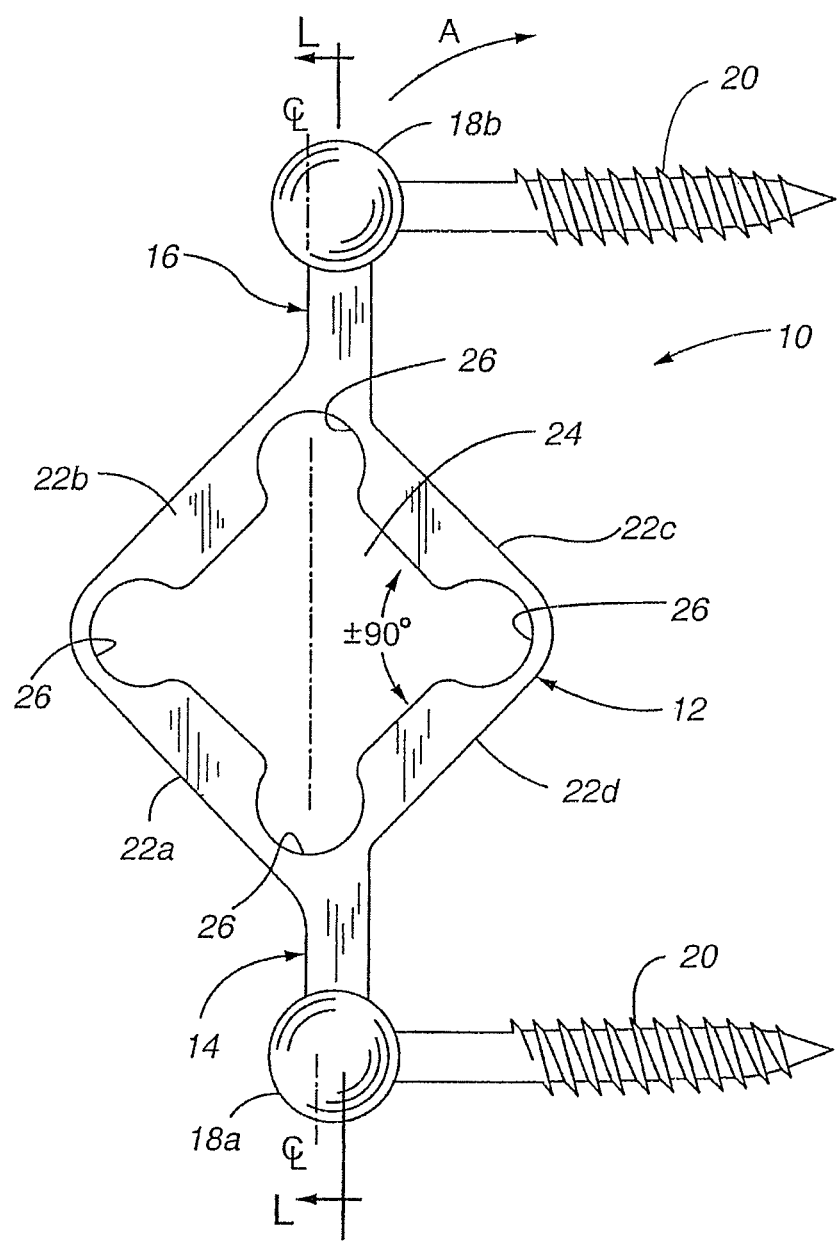
FIG. 3a is a side elevation view of a first embodiment of a dynamic fixation device used in conjunction with pedicle screws.

Referring now to FIG. 3a, a side elevation view of a first embodiment of a dynamic fixation device 10 is illustrated. The dynamic fixation device 10 includes a geometric shape 12 connected to a first rod end 14 and a second rod end 16. First rod end 14 and second rod end 16 are preferably connected to connectors 18a and 18b that, in turn, are connected to pedicle screws 20. Pedicle screws 20 are inserted into the pedicles of vertebrae when the device is attached to the vertebrae of a patient. Connectors 18a and 18b can be of the type that are integrally formed as part of first rod end 14 and second rod end 16, respectively. Alternately, one or both of the connectors can be a separate type of connector that can be selectively positioned along the length of first rod end 14 or second rod end 16, respectively, such that first rod end 14 and second rod end 16 are adjustable (e.g., slidably) within the connectors prior to tightening the connectors to fixedly interconnect the device 10 to the pedicle screws 20.

Still referring to FIG. 3a, dynamic fixation device 10 is shown in a neutral position. As noted, the dynamic fixation device 10 includes a geometric shape 12 between first rod end 14 and second rod end 16. More specifically, in one embodiment dynamic fixation device 10 includes a substantially rectangular or substantially diamond-shaped geometric shape 12 that has four arms 22a, 22b, 22c and 22d. To the interior of arms 22a, 22b, 22c, and 22d is hollow region or opening 24. In lieu of an open space, opening 24 can be formed of and/or covered by a flexible or an elastic-type webbing material (not shown).

In a separate aspect dynamic fixation device 10, the centerline of geometric shape 12 is offset relative to the longitudinal axis of dynamic fixation device 10. More particularly, as shown in FIG. 3a, dynamic fixation device 10 has a longitudinal axis L-L that passes through the centerline of first rod end 14 and second rod end 16. However, the centerline CL-CL of geometric shape 12 is offset posteriorly to the longitudinal axis L-L of dynamic fixation device 10. This offset provides a preference for the dynamic fixation device 10 to bend in flexion, but resist bending in extension.

It is an aspect of this embodiment that the arms 22a, 22b, 22c, and 22d of geometric shape 12 are situated desired angles (e.g., at approximately 90 degree angles) relative to each other when device 10 is in the neutral position. For example, arm 22a is situated at an angle of about 90 degrees relative to arm 22b and arm 22d. Likewise, arm 22c is situated at an angle of about 90 degrees relative to arm 22b and arm 22d. Upon deformation of geometric shape 12 due to flexion of the spine, geometric shape 12 deforms and the angles between the arms will change.

Still referring to FIG. 3a, in yet a separate aspect of dynamic fixation device 10 the convergence segments 26 between the arms includes reduced dimensions. More particularly, the dimensions of arms 22a and 22b are smaller in the vicinity where arm 22a joins arm 22b. Likewise, the dimension of arms 22b and 22c are also smaller in the vicinity where arm 22b joins arm 22c. This is also the case for the convergence segments between arms 22c and 22d, and between arms 22d and 22a. The decreased dimensions of the arms 22a, 22b, 22c and 22d at the convergence segments 26 allow additional flexibility between the arms. As shown in FIG. 3a, the convergence segments 26 include partially circular corners between the arms. Alternatively, the partially circular corners may be of a different shape, such as partially triangular (not shown). Thus, dynamic fixation device 10 preferably includes narrowing or thinning of the arms in the vicinity of the convergence segments 26. It is to be further noted that convergence segments 26 serve as elastomeric hinges for geometric shape 12.

Figure 3B:
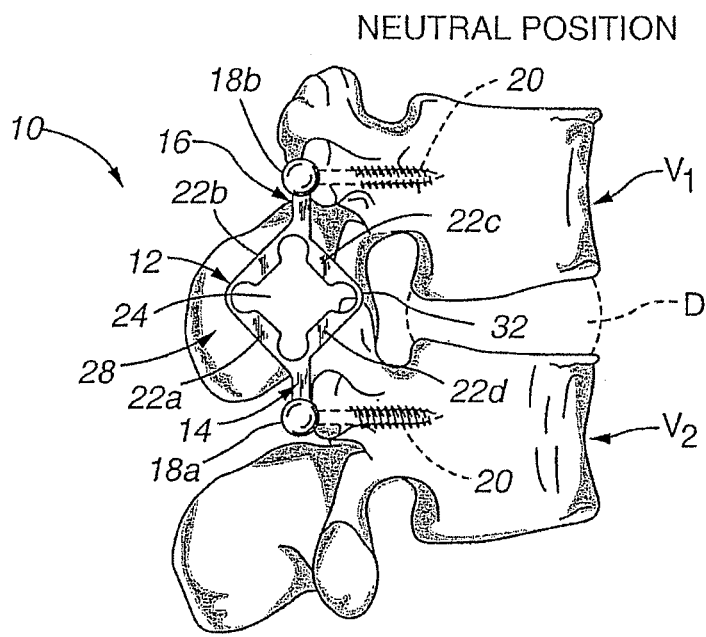
FIG. 3b is a side perspective view of the device shown in FIG. 3a attached to two vertebra in a neutral position.
Figure 3C:
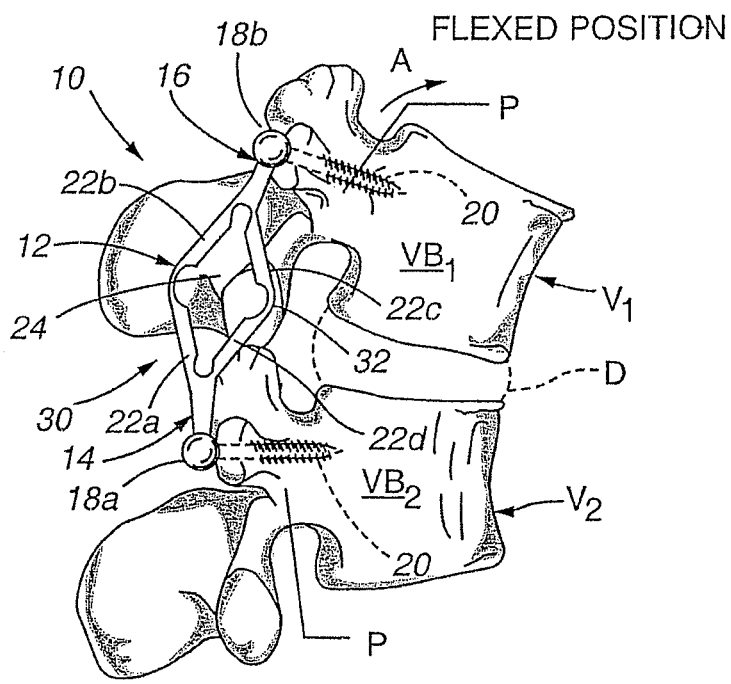
FIG. 3c is a side perspective view of the device shown in FIG. 3a attached to two vertebra in a flexed position.

As shown in the example illustrated in FIGS. 3b and 3c, first rod end 14 is shown to remain essentially immobile. Second rod end 16 moves between a neutral or first position 28, as shown in FIG. 3b, and a flexed or second position 30, as shown in FIG. 3c. In moving between first position 28 and second position 30 dynamic fixation device 10 elongates and it also rotates about an effective pivot point 32. The geometric shape 12 provides an effective pivot point 32 that is forward or anterior of the longitudinal axis L-L of first rod end 14 and second rod end 16. During movement between first position 28 and second position 30, dynamic fixation device 10 experiences deformation, whereby it bends and it elongates.

In use, a surgeon first makes an incision and then inserts pedicle screws 20. Subsequently, first rod end 14 and second rod end 16 of dynamic fixation device 10 are preferably interconnected using connectors 18a and 18b to pedicle screws 20 that are inserted into vertebrae $V_1$ and $V_2$ of the spine. During flexion and extension, each vertebra exhibits an arcuate motion in relation to the vertebra below. The center of the arc lies below the moving vertebra. Dynamic fixation device 10 provides a device for allowing movement of the upper vertebra $V_1$ to a flexed or second position 30, with a forwardly or anteriorly projected pivot location 32, as compared to the location of the longitudinal axis L-L of the device 10 when it is in the neutral position.

In a modification of the embodiment shown in FIG. 3a, the geometric shape 12 can be subdivided into four smaller rectangles (not shown) as opposed to one large rectangle. This modification of using four smaller rectangles to form a geometric shape still acts as a larger rectangle in terms of its effective pivot point. In yet an alternate modification of this embodiment, geometric shape 12 can take the form of a rhomboid (not shown). In this modification, an effective pivot point would be projected forward (or anterior) some distance of the dynamic fixation device. Accordingly, depending upon its construction, the geometric shape 12 allows the pivot point to extend beyond the limits of the device. When the dynamic fixation device 10 is implanted posterior the spinal vertebrae, the device nonetheless allows for a rotation point substantially anterior the device. Thus, depending upon the geometry of the dynamic fixation device, and more particularly, the geometry of geometric shape 12, the present invention allows an effective pivot point 32 to be created that substantially corresponds to the natural pivot point of the patient's spine.

Figure 4A:
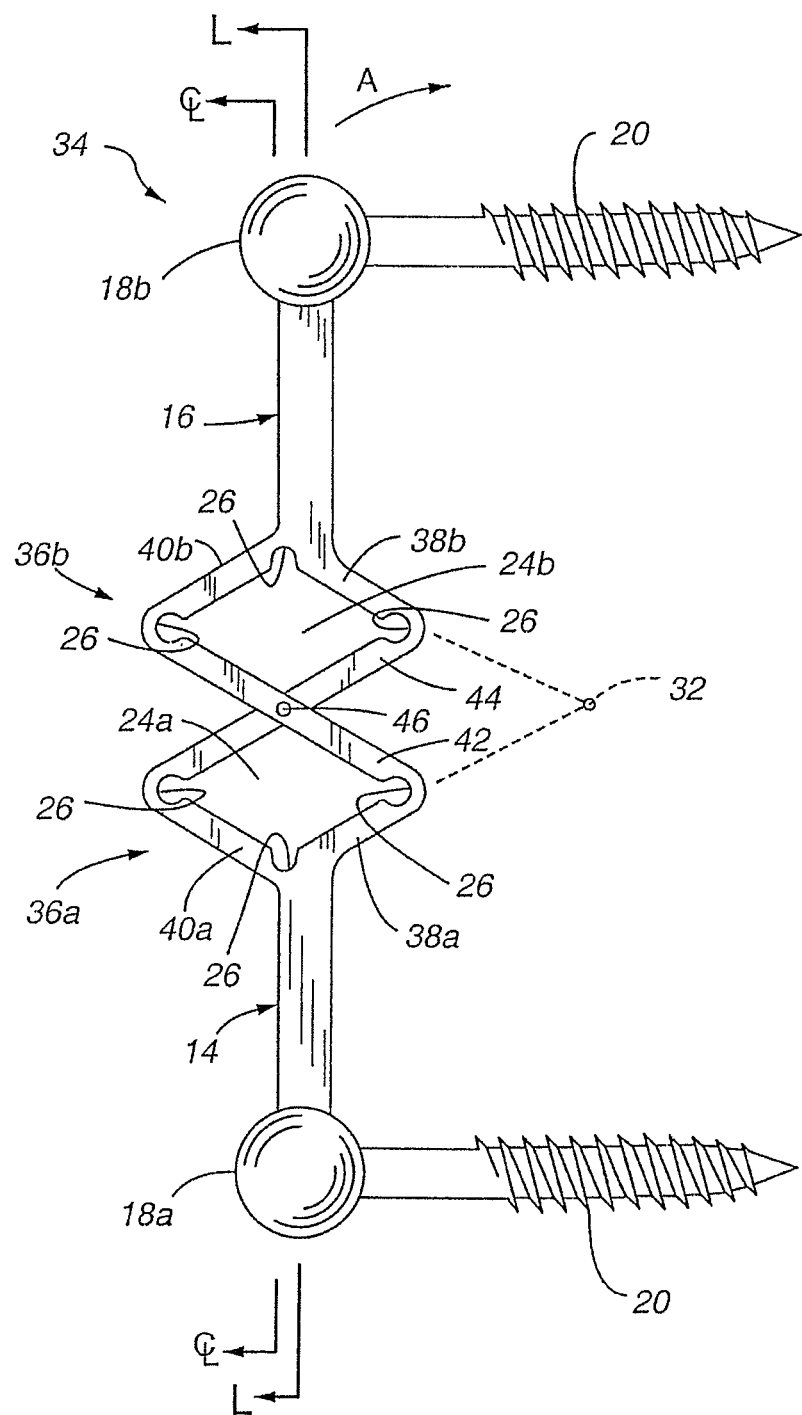
FIG. 4a is a side elevation view of a separate embodiment of a dynamic fixation device used in conjunction with pedicle screws.

Referring now to FIG. 4a, a side elevation view of a separate embodiment of a dynamic fixation device 34 is shown. The dynamic fixation device 34 of FIG. 4a utilizes two adjacent but connected substantially geometric shapes 36a and 36b. Substantially geometric shapes 36a and 36b act as two accordion shapes that expand and flexibly bend forward as dynamic fixation device 34 is elongated and rotated during bending of the spine. Arrow A depicts the general direction of motion of second rod end 16 during rotation and elongation of the dynamic fixation device 34.

Still referring to FIG. 4a, in one preferred embodiment, substantially geometric shapes 36a and 36b include a plurality of arms. Substantially geometric shape 36a includes an anterior arm 38a and a posterior arm 40a. Similarly, substantially geometric shape 36b includes an anterior arm 38b and a posterior arm 40b. Preferably, anterior arm 38a interconnects to posterior arm 40b by crossing arm 42. Similarly, anterior arm 38b interconnects to posterior arm 40a by crossing arm 44. Although not required, crossing arm 42 can be hingedly connected to crossing arm 44 using a pin 46 positioned along crossing arm 42 and crossing arm 44. As with dynamic fixation device 10 described above, narrowing or thinning of the arms in the vicinity of the convergence segments 26 is preferred. An opening 24a exists between crossing arm 42, anterior arm 38a and posterior arm 40a of substantially geometric shape 36a, and another opening 24b exists between crossing arm 44, anterior arm 38b and posterior arm 40b. In lieu of an open space, openings 24a and 24b can be formed of a flexible or an elastic-type webbing material (not shown).

Figure 4B:
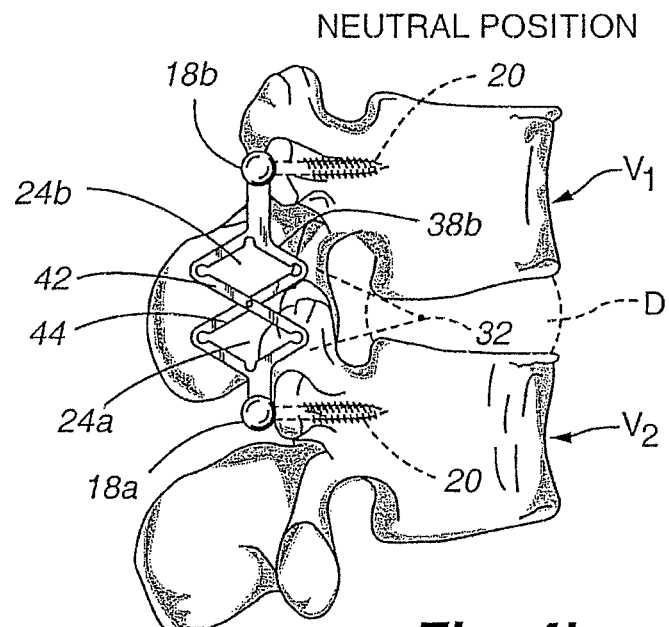
FIG. 4b is a side perspective view of the device shown in FIG. 4a attached to two vertebra in a neutral position.
Figure 4C:
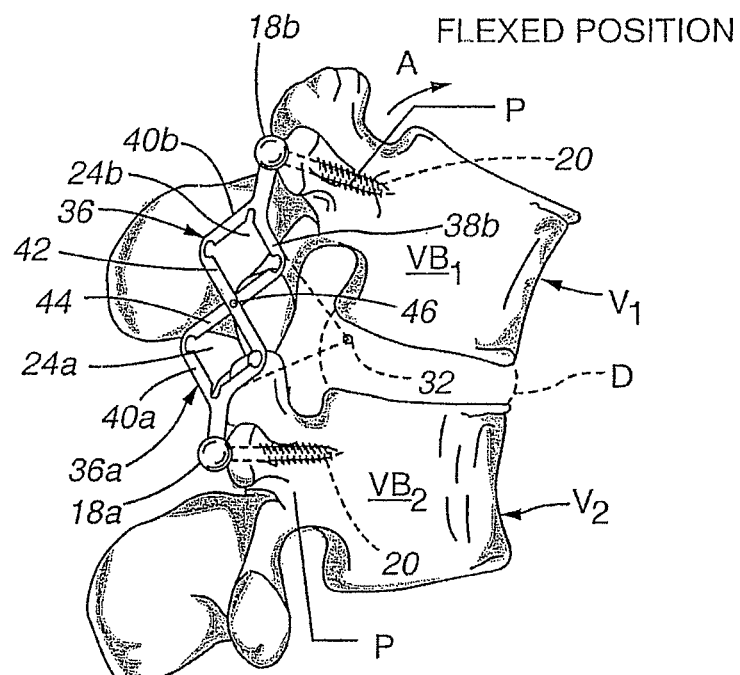
FIG. 4c is a side perspective view of the device shown in FIG. 4a attached to two vertebra in a flexed position.

FIGS. 4b and 4c show dynamic fixation device 34 in its neutral and flexed positions, respectively. The effect of the substantially geometric shapes 36a and 36b is to produce an anteriorly projected effective pivot point 32 that substantially matches the rotational point of the vertebrae to which it is attached. Thus, the device of FIGS. 4a-4c substantially limits translational displacement of the vertebrae to which it is attached, while still allowing some amount of flexion. In general, the bending occurring with flexion is equal to the angle change between anterior arm 38a and anterior arm 38b as the construct elongates. Preferably, there is a rigid connection between first rod end 14 and anterior arm 38a, as well as a rigid connection between second rod arm 16 and anterior arm 38b.

In a separate aspect dynamic fixation device 34, the centerline of substantially geometric shapes 36a and 36b is offset posteriorly relative to the longitudinal axis of dynamic fixation device 34. More particularly, as shown in FIG. 4a, dynamic fixation device 34 has a longitudinal axis L-L that passes through the centerline of first rod end 14 and second rod end 16. However, the centerline CL-CL of substantially geometric shape 36a and 36b is offset posteriorly to the longitudinal axis L-L of dynamic fixation device 34. This offset provides a natural fixation for the first rod end 14 to be a continuation of anterior arm 38a, and for second rod end 16 to be a continuation of anterior arm 38b.

Figure 5A:
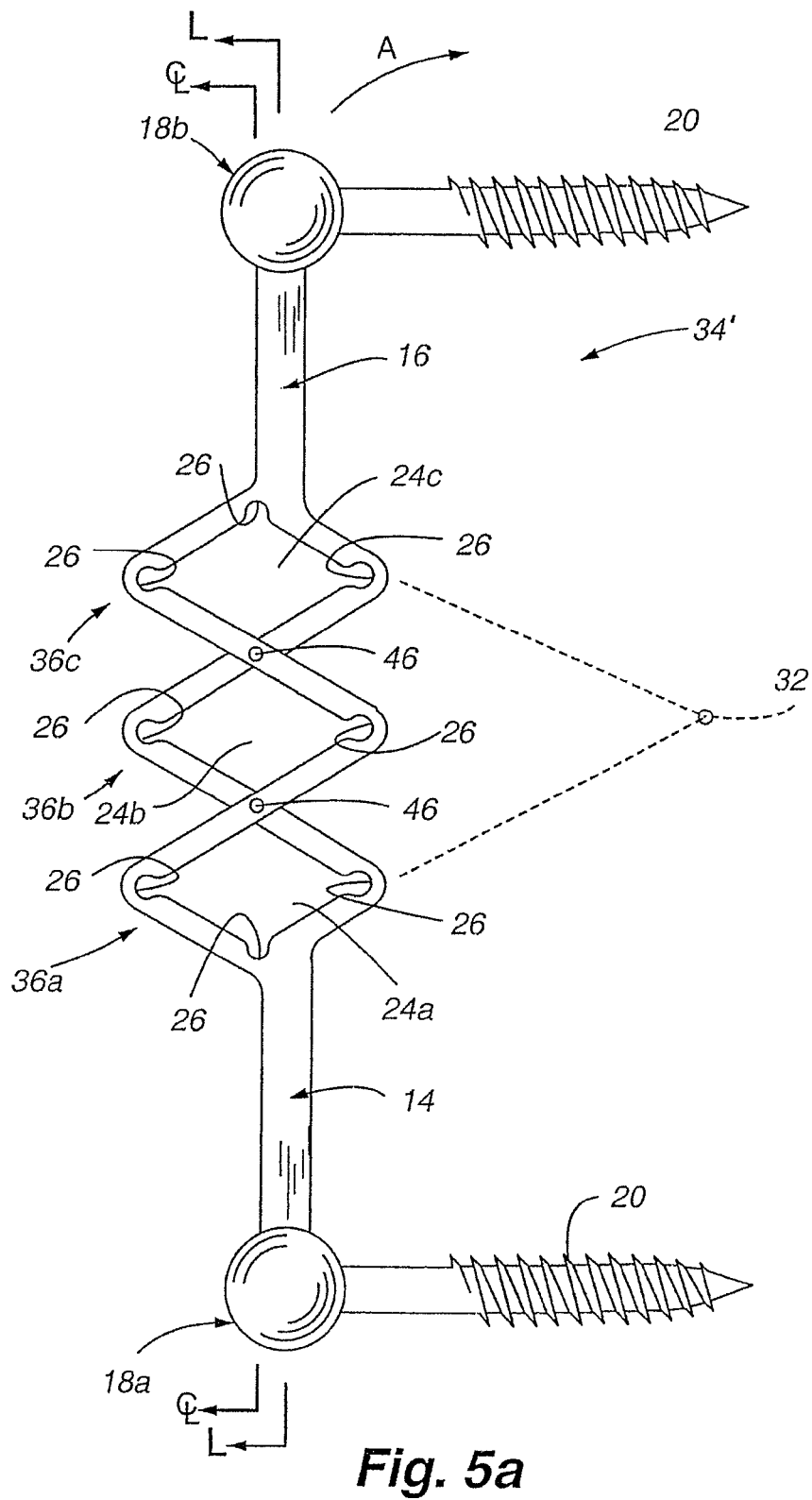
FIG. 5a is a side elevation view of a modification of the dynamic fixation device shown in FIG. 4a used in conjunction with pedicle screws.

Referring now to FIG. 5a, in a modification of the embodiment shown in FIG. 4a, more than two substantially geometric shapes may be incorporated into a dynamic fixation device 34'. More particularly, the dynamic fixation device 34 having substantially geometric shapes 36a and 36b may be modified to include a third, fourth, fifth, or any number of additional substantially geometric shapes. For example, substantially geometric shapes 36a and 36b of the device shown in FIG. 4a illustrate two substantially diamond shaped features, respectively. However, as shown in FIG. 5a, a third substantially diamond shape 36c may be added to geometric shape 36a and 36b. Optional pins 46 may be used between the various substantially geometric shapes. Alternatively, four (not shown), five (not shown) or more geometric shapes may be grouped together to form a dynamic fixation device. Multiple substantially geometric shapes may differ in size and/or overall shaped configuration, which may be desirous depending upon the number used. For example, where three substantially geometric shapes 36a, 36b and 36c are used, as in dynamic fixation device 34', the overall size of each geometric shape is preferably smaller than the two substantially geometric shapes 36a and 36b illustrated in dynamic fixation device 34, as shown in FIG. 4a. The, addition of added substantially geometric shapes projects the pivot pint 32 proportionally forward for the number of substantially geometric shapes used.

Referring now to FIGS. 6a-6f, in yet a separate embodiment of the invention, a dynamic fixation device 50 includes geometric shape 12 with an interior hollow region 24, wherein device 50 bends in a direction transverse to the planar surface 52 of geometric shape 12. The interior hollow region 24 preferably includes sloped interior surface 54. That is, the interior sidewalls 56 have an interior surface 54 that is at an angle θ. with the planar surface 52 of geometric shape 12. Angle θ of interior surface 54 can be one constant value, or it can vary within the device. By way of a non-limiting example, θ can be 60 degrees at the top of device 50, and vary to about 90 degrees at the bottom of device 50.

Figure 6A:
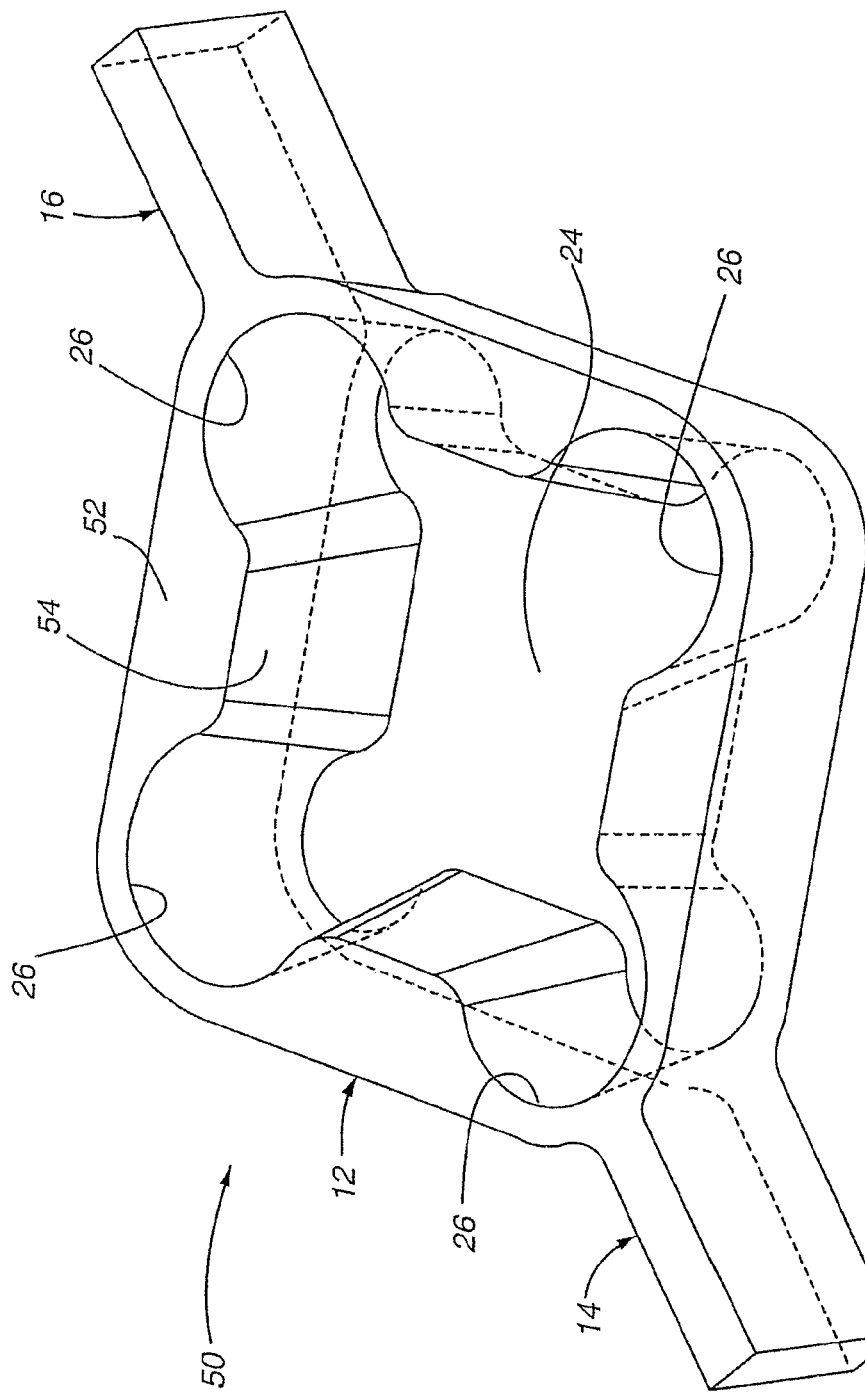
FIG. 6a is a front perspective view of a separate embodiment of a dynamic fixation device.
Figure 6C:
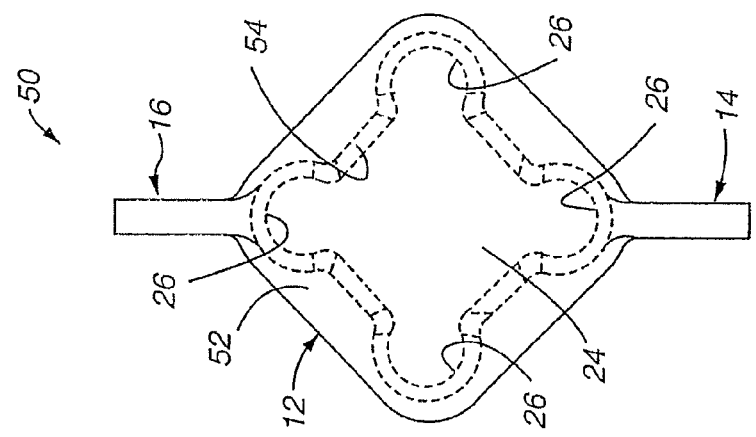
Figure 6D:
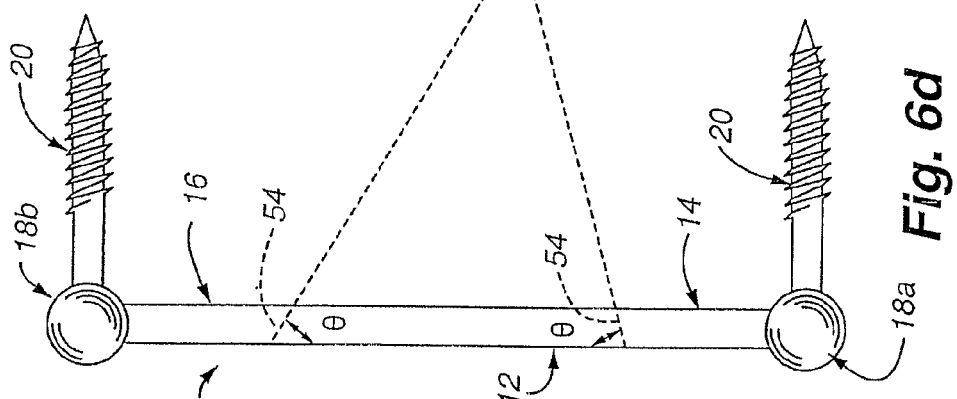
Figure 6B:
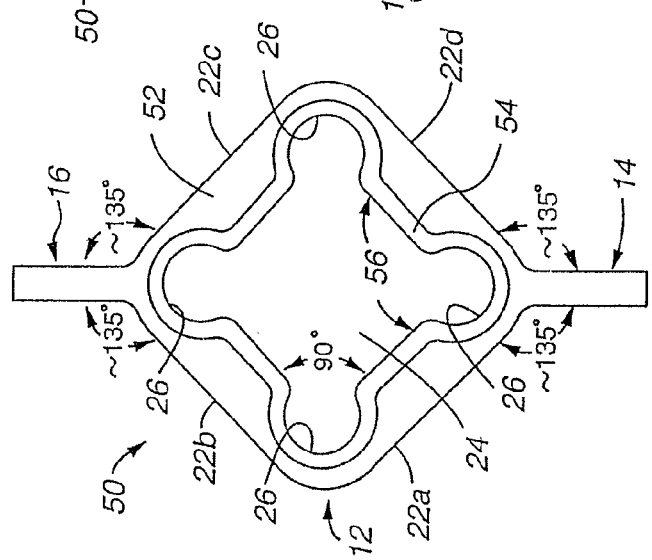
Figure 6E:
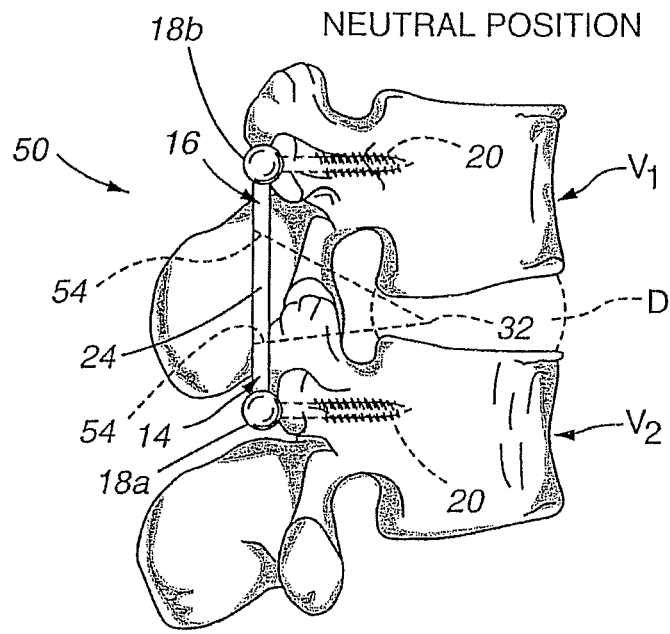
FIG. 6e is a side perspective view of the device shown in FIG. 6a attached to two vertebra in a neutral position.
Figure 6F:
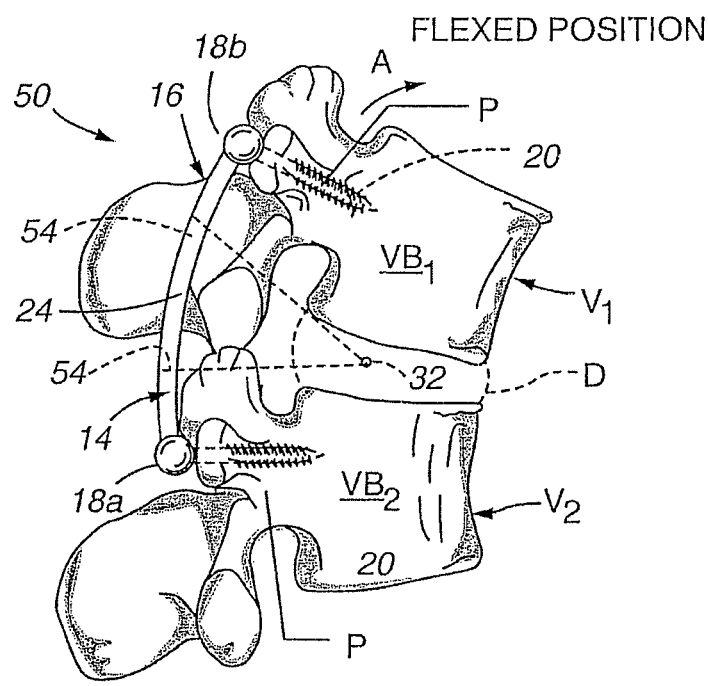
FIG. 6f is a side perspective view of the device shown in FIG. 6a attached to two vertebra in a flexed position.

Referring now to FIGS. 6a-6c, interior hollow region 24 preferably includes four partially circular corners or convergence segments 26. Attached to two opposing partially circular corners or convergence segments 26 are first rod end 14 and second rod end 16. Each rod end 14 and 16 is situated at an angle of about 135 degrees from each adjacent side of the geometric shape 12. However, in an alternate aspect of this embodiment, the rod ends 14 and 16 may be situated at different angles relative to the arms of the geometric shape 12. As with device 10, partially circular corners or convergence segments 26 may be of a different shape, such as partially triangular. Equivalently, a mechanical hinge rather than an elastomeric hinge may be incorporated at convergence segments 26.

As shown in FIG. 6d, pedicle screws 20 are orientated perpendicular to the planar surface 52 of geometric shape 12. Connectors 18a and 18b are used to attach the pedicle screws 20 to first and second rod ends 14 and 16 of dynamic fixation device 50. The connectors 18a, 18b may be formed as an integral part of dynamic fixation device 50, or the connectors 18a, 18b may be a separate device, as is known to those knowledgeable in the art. In use, the dynamic fixation device 50 expands as it rotates and/or bends when attached to two vertebra that undergo flexion.

Figure 7A:
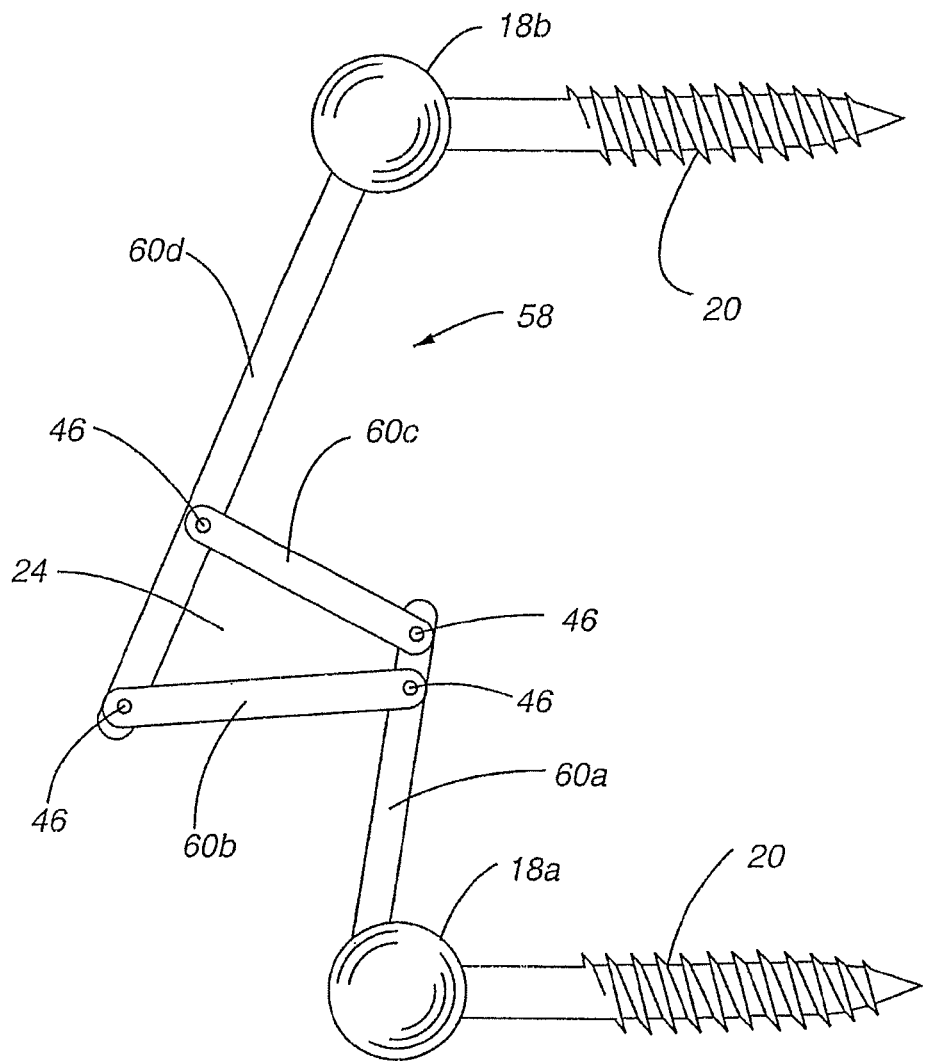
FIG. 7a is a side elevation view of a separate embodiment of a dynamic fixation device used in conjunction with pedicle screws.
Figure 7B:
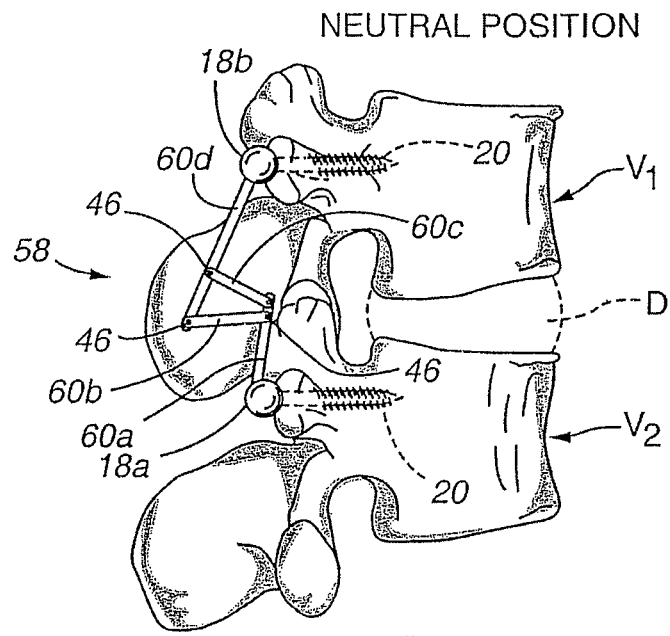
FIG. 7b is a side perspective view of the device shown in FIG. 7a attached to two vertebra in a neutral position.
Figure 7C:
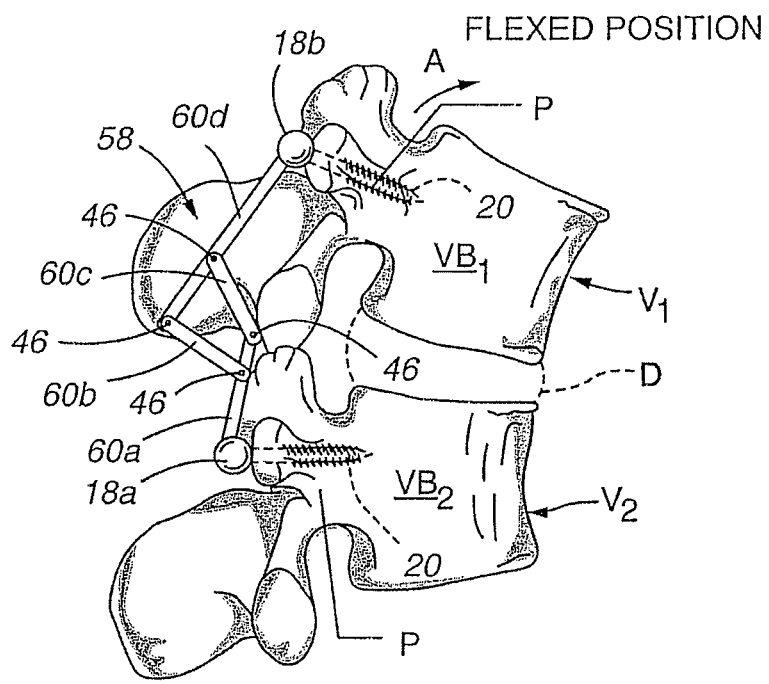
FIG. 7c is a side perspective view of the device shown in FIG. 7a attached to two vertebra in a flexed position.

Referring now to FIGS. 7a-7c, yet a separate embodiment of a dynamic fixation device is shown. Dynamic fixation device 58 includes four substantially straight and rigid arm segments. These consist of lower arm 60a, first middle arm 60b, second middle arm 60c, and upper arm 60d. Lower arm 60a and upper arm 60d connect to connectors 18a and 18b, respectively, which are then connected to pedicle screws 20. Using pins 46, lower arm 60a is hingedly connected to one end of middle arms 60b and 60c. Upper arm 60d is hingedly connected using pins 46 to the opposite end of middle arms 60b and 60c. Between the four hinge points is an opening 24 that is a quadrilateral shape. During flexion, upper arm 60d moves upward and forward, thereby forcing middle arms 60b and 60c to rotate downward. Thus, the hinged connection of middle arms 60b and 60c to upper arm 60d allows it to move forward, while the connection of middle arms 60b and 60c to lower arm 60a prevents excessive translation or over-rotation. Dynamic fixation device 58 allows for the upper vertebra to move up and forward, yet resists excessive translation of the vertebrae to which it is attached.

Figure 8A:
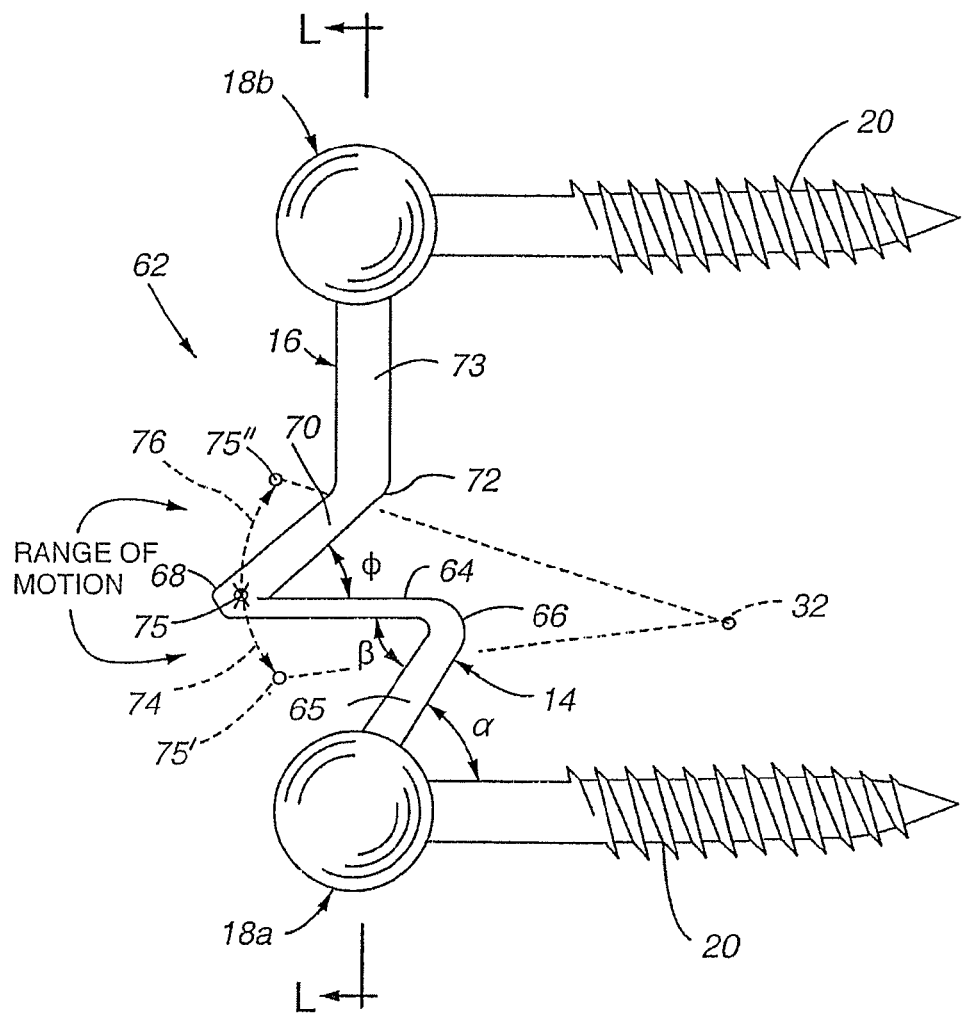
FIG. 8a is a side elevation view of a separate embodiment of a dynamic fixation device used in conjunction with pedicle screws.

Referring now to FIG. 8a, yet a separate embodiment of a dynamic fixation device is shown. The dynamic fixation device 62 shown in FIG. 8a is a dynamic fixation device that features an anterior-posterior segment 64. The dynamic fixation device 62 includes a first rod end 14 having a rod arm 65 that extends at an angle α toward an anterior-posterior segment 64. Angle α is fixed in relation to pedicle screw 20 by the rigid connection between rod arm 65 and lower pedicle screw 20. Similarly, rod arm 73 is fixed by a rigid connection to the upper pedicle screw 20. Rod arm 65 of first rod end 14 is connected to anterior-posterior segment 64 at bend 66. More particularly, bend 66 forming the connection between rod arm 65 and anterior-posterior segment 64 can be a continuous structural piece such that rod arm 65 and anterior-posterior segment 64 are essentially a contiguous solid piece including bend 66. Alternatively, bend 66 may be a hinged connection with a pin that interconnects rod arm 65 to anterior-posterior segment 64. Anterior-posterior segment 64 is separated from rod arm 65 by angle β.

Still referring to FIG. 8a, at bend 66, anterior-posterior segment 64 extends posteriorly to bend 68. Middle rod segment 70 extends from bend 68 at the posterior end of anterior-posterior segment 64 to bend 72 that forms the connection to rod arm 73 of second rod end 16. Bend 72 forms the intersection and the connection between middle rod segment 70 and rod arm 73. Bend 72 can be a continuous structural piece such that middle rod segment 70 and rod arm 73 are essentially a contiguous solid piece including bend 72, or bend 72 can be a connection that interconnects middle rod segment 70 and rod arm 73. The middle rod segment 70 is separated from the anterior-posterior segment 64 by angle Φ.

First rod end 14 and second rod end 16 preferably are interconnected to pedicle screws 20 using connectors 18a and 18b, respectively. Connectors 18a and 18b can be formed as an integral part of the end of dynamic fixation device 62, or they can be separate devices, as is known to those knowledgeable in the art.

Still referring to the example of the present embodiment shown in FIG. 8a, dynamic fixation device 62 also has a longitudinal axis L-L that is defined by the center of connectors 18a and 18b. Rod arm 65 generally lies anterior of longitudinal axis L-L, and middle rod segment 70 generally lies posterior of longitudinal axis L-L, with anterior-posterior segment 64 having portions both on the anterior and posterior sides of longitudinal axis L-L.

It is an aspect of the present embodiment that bend 68 preferably acts as a hinge and is able to move down if the vertebrae to which the dynamic fixation device 62 is attached is placed in compression. In addition, bend 68 can move up to accommodate flexion of the vertebrae. This motion of bend 68 and the anterior-posterior segment 64 closely approximates the normal arc of motion of human vertebra. When in compression, bend 68 moves down along a lower arc path 74. Lower arc path 74 is caused when dynamic fixation device 62 is placed in compression and anterior-posterior segment 64 moves toward rod arm 65, thereby decreasing the angle β. In a typical human patient, angle β may decrease up to 30 degrees as bend 68 passes along lower arc path 74. To achieve this motion, bend 68 of dynamic fixation device 62 preferably includes a structure to allow it to act as a hinge. Accordingly, bend 68 may include a pin 75. As illustrated in FIG. 8a, pin 75 is shown in the neutral position. However, in the compressed position, pin 75' is shown in its lower position. When the vertebrae undergo flexion, bend 68 moves up along an upper arc path 76. Upper arc path 76 is caused when dynamic fixation device 62 elongates and anterior-posterior segment 64 moves upward, thereby increasing the angle β. In a typical human implant, angle β may increase up to 30 degrees as bend 68 passes along upper arc path 76. For at least some patients, the neutral position for anterior-posterior segment 64 will be slanted downward from horizontal, with bend 68 positioned lower than bend 66. Thus, angle β would have a lesser amount of allowable compression over flexion extension. In the elongation condition, pin 75" is shown in its upper position. In compression, angle Φ will decrease, and when the dynamic fixation device elongates during flexion, angle Φ will increase.

The various embodiments of the present invention allows a slight amount of translational motion of the vertebrae, but the amount of translational motion allowed is within the physiological limits of normal motion of the human vertebrae. For example, for the embodiment shown in FIG. 8*a*, as pin 75 moves forward along lower arc path 74 and upper arc path 76, the vertebrae will undergo a slight amount of translational movement, as is evidenced by the position of pin 75' and 75", which are moved slightly anterior or forward from the neutral position.

Figure 9A:
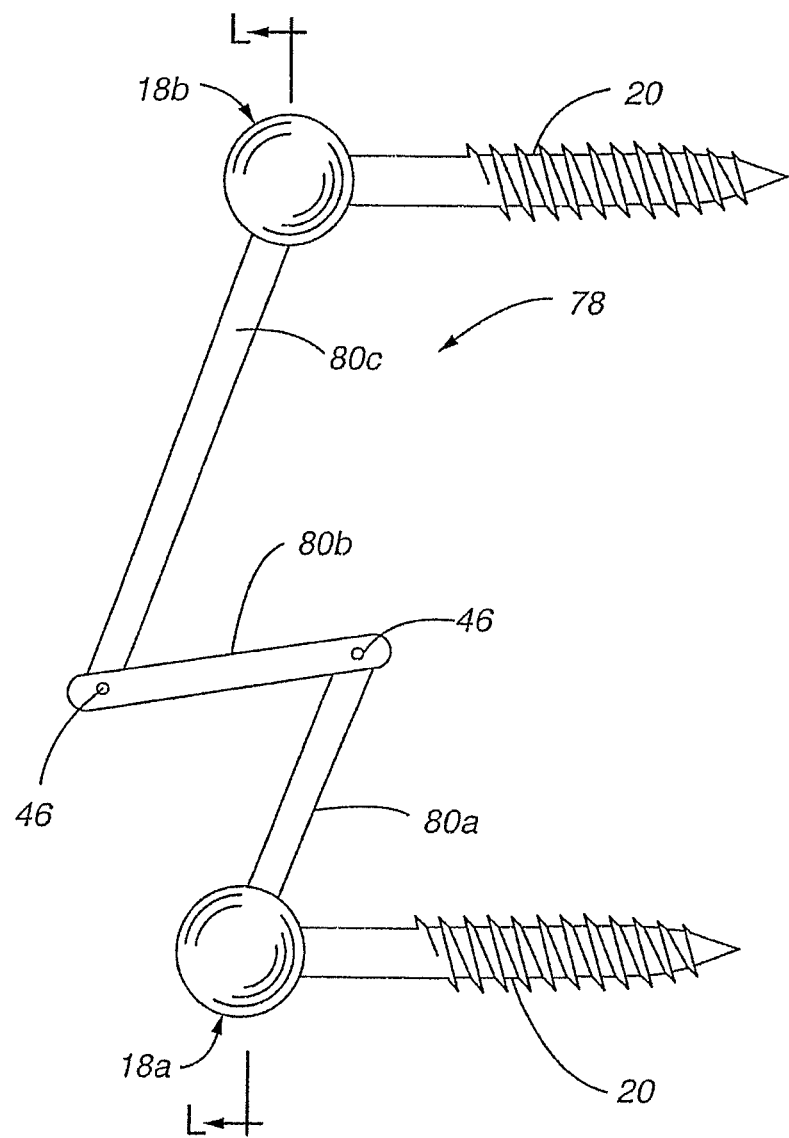
FIG. 9a is a side elevation view of a separate embodiment of a dynamic fixation device used in conjunction with pedicle screws.
Figure 9B:
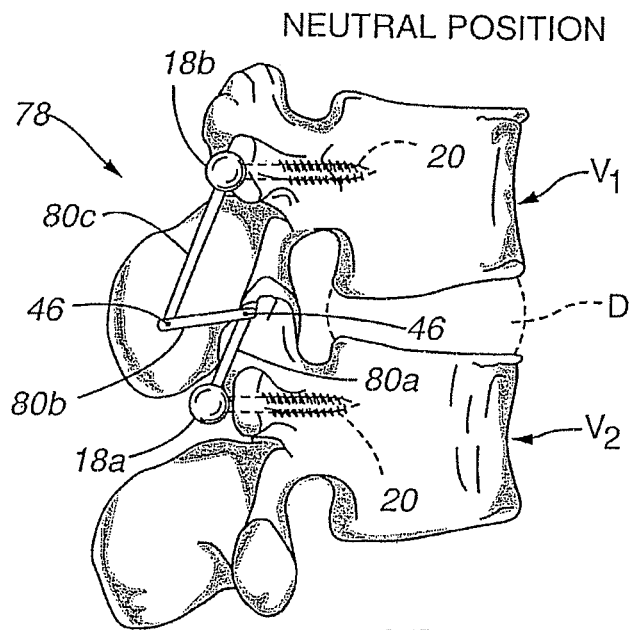
FIG. 9b is a side perspective view of the device shown in FIG. 9a attached to two vertebra in a neutral position.
Figure 9C:
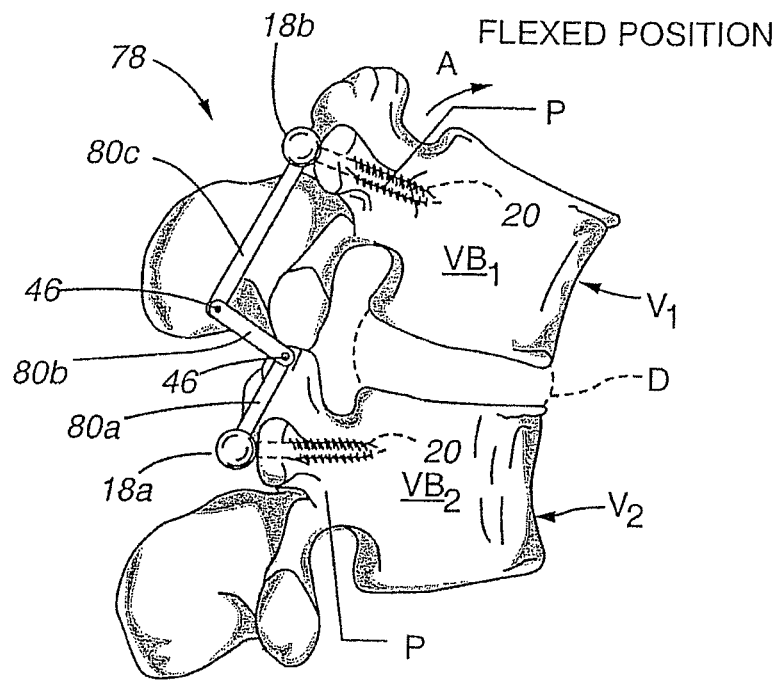
FIG. 9c is a side perspective view of the device shown in FIG. 9a attached to two vertebra in a flexed position.

Referring now to FIGS. 9*a*-9*c*, yet a separate embodiment of a dynamic fixation device is shown. Dynamic fixation device 78 includes three substantially straight arm segments. These consist of lower arm 80*a*, first middle arm 80*b*, and upper arm 80*c*. Lower arm 80*a* and upper arm 80*c* connect to connectors 18*a* and 18*b*, respectively, which are then connected to pedicle screws 20. Using a pin 46, lower arm 80*a* is hingedly connected to one end of middle arm 80*b*. The opposite end of middle arm 80*b* is hingedly connected (e.g., by a pin 46) to upper arm 80*c*. During flexion, upper arm 80*c* moves upward and forward, thereby forcing middle arm 80*b* to rotate downward. Thus, the hinged connection of middle arm 80*b* to upper arm 80*c* allow it to upward with forward rotation, while the connection between middle arm 80*b* and lower arm 80*a* prevents excessive translation or over-rotation. Similar to function of the anterior-posterior segment 64 in device 62, middle arm 80*b* in the present embodiment acts as an anterior-posterior segment that allows a range of motion in flexion, yet prevents the vertebrae from experiencing excessive translation. Thus, dynamic fixation device 78 allows for the upper vertebra to move up and slightly forward, yet resists excessive translation of the vertebrae to which it is attached.

Figure 10A:
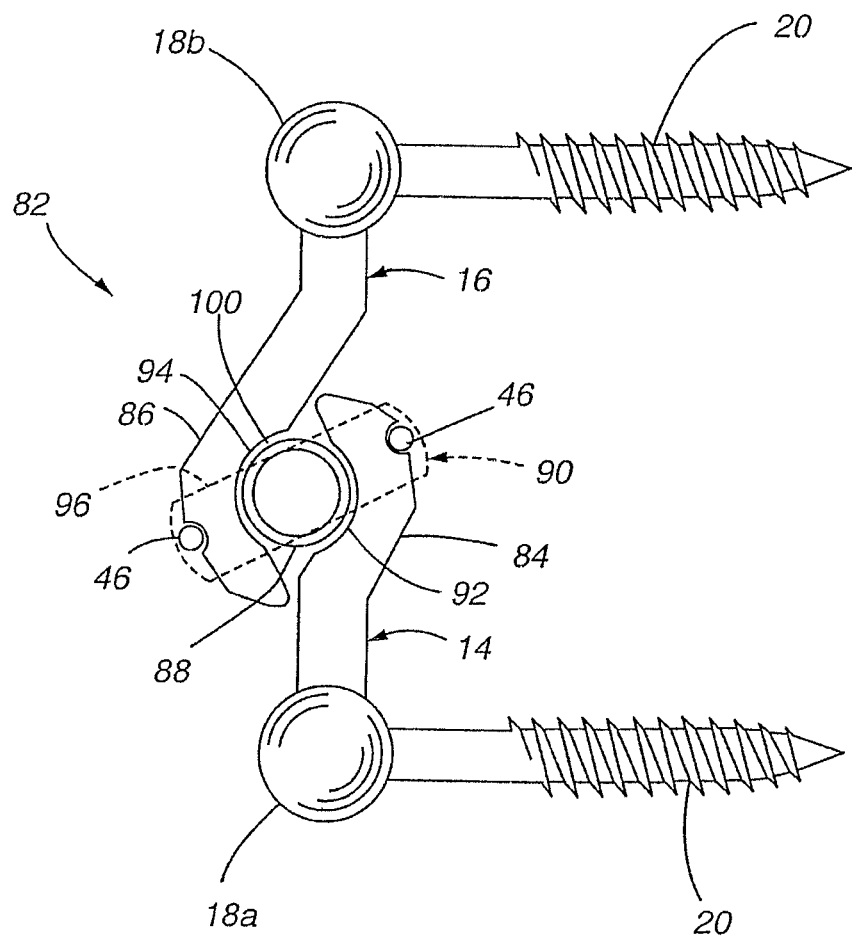
FIG. 10a is a side elevation view of a separate embodiment of a dynamic fixation device used in conjunction with pedicle screws.

Referring now to FIG. 10*a*, yet a separate embodiment of a dynamic fixation device is illustrated. Dynamic fixation device 82 includes a first rod member 84 connected to a first rod end 14 and a second rod member 86 connected to a second rod end 16, wherein the first rod end 14 and the second rod end 16 are interconnected to pedicle screws 20 using connectors 18*a* and 18*b*, respectively. First rod member 84 and second rod member 86 anteriorly and posteriorly confine a spring 88. In addition, rails 90 confine spring 88 on the lateral sides, and rails 90 also serve to interconnect first rod member 84 to second rod member 86. The structure of dynamic fixation device 82 provides for an articulated device that can also elongate, thus accommodating the natural physiologic motion of two adjacent vertebra when undergoing flexion. The structure and function of these components will be described in detail below.

Still referring to FIG. 10*a*, first rod member 84 preferably includes a concave surface 92 along its posterior side, wherein the concave surface 92 of first rod member 84 assists in providing anterior confinement of spring 88. Second rod member 86 preferably includes a concave surface 94 along its anterior side, wherein the concave surface 94 of second rod member 86 assists in providing posterior confinement of spring 88.

Figure 10B:
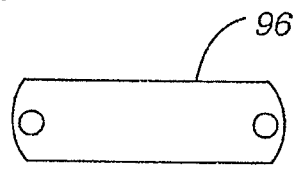

As noted above, rails 90 (shown in dashed lines) interconnect the first rod member 84 to second rod member 86. Preferably, rails 90 comprise a plate 96 with hinge pins 46 situated through both ends of the plate 96. Plate 96 is shown in FIG. 10*b*. In one preferred embodiment, first rod member 84 includes a first notch 98 for receiving a first hinge pin 46. Similarly, second rod member 86 includes a second notch 98 receiving a second hinge pin 46. Plates 96 span the confinement zone 100 of spring 88 and interconnect first rod member 84 and second rod member 86 while laterally containing spring 88 between rod members 84 and 86 and preventing the spring 88 for moving outside of the confinement zone 100. In a separate aspect of the present embodiment, rails 90 may be formed using a single piece. That is, the plate 96 and hinge pin 46 construction may be machined or otherwise constructed of a single piece.

By way of example and not limitation, preferably spring 88 is a cylindrical shaped spring having a proper spring constant for the dynamic fixation device 82. In addition, spring 88 may also take the form of a resilient material, such as a properly sized silicone insert shaped, for example, as a disc or a sphere. During flexion motion of the spine, second rod member 86 moves up and forward. During this movement, the spring 88 rolls between the first rod member 84 and the second rod member 86. Since the spring 88 rolls, friction between first rod member 84 and second rod member 86 is minimal. Thus, the ability of the spring to roll can be modified by adjusting the shape of the spring and the shape and texture of the interior walls of the confinement zone 100. More particularly, the shape and surface texture of concave surfaces 92 and 94 of the first and second rod members 84 and 86, respectively, can be modified to adjust the magnitude and ease of motion in elongation of the second rod member 86 relative to the first rod member 84. Since the spring 88 is cable of being compressed, it deforms, thereby allowing bending. The amount of compression is controlled by the spring characteristics, such as the spring material type, diameter and wall thickness, as well as the shape of the confinement zone 100 and the texture of the concave surfaces 92 and 94. With regard to the shape of the confinement zone 100, the concave surfaces 92 and 94 serve as the compression surfaces of the confinement zone 100 for spring 88. The shape of the curves of the concave surfaces 92 and 94 can be altered to control the degree of spring compression as the construct elongates. For example, referring to FIG. 10*a*, the curvature of concave surfaces 92 and 94 can be flattened, thereby influencing the reaction of the spring 88 within the confinement zone 100 during flexion extension.

Figure 10C:
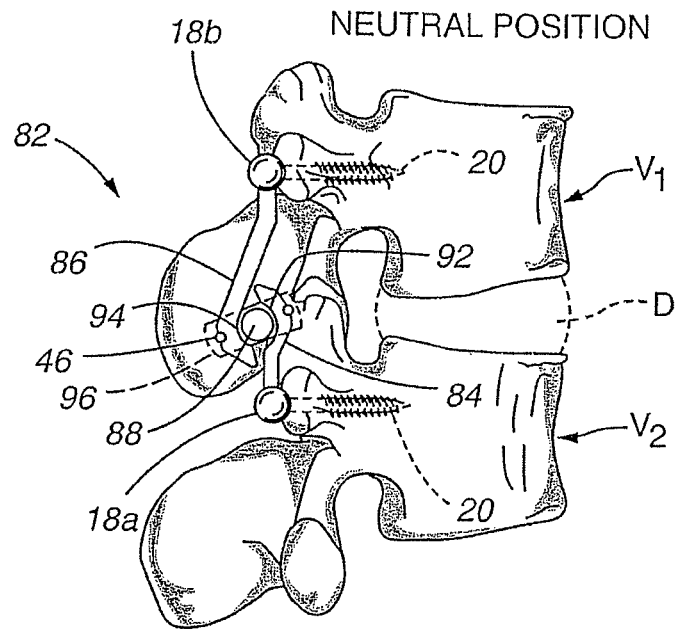
FIG. 10c is a side perspective view of the device shown in FIG. 10a attached to two vertebra in a neutral position.
Figure 10D:
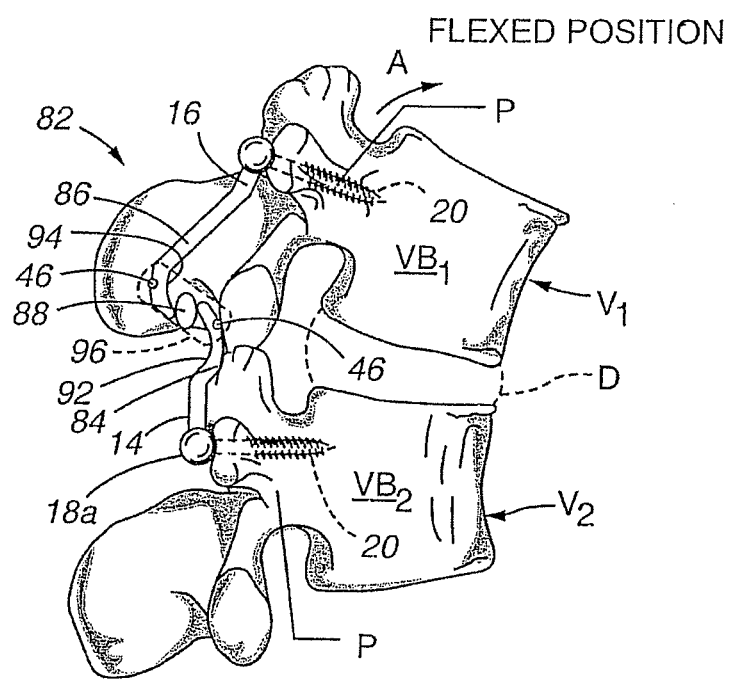
FIG. 10d is a side perspective view of the device shown in FIG. 10a attached to two vertebra in a flexed position.

Referring now to FIGS. 10*c* and 10*d*, dynamic fixation device 82 is shown both in its neutral position and it the flexed position, respectively. For purposes of clarity, the rails 90 are dashed in FIGS. 10*c* and 10*d*. As compared to the neutral position shown in FIG. 10*c*, the elongated position of FIG. 10*d* illustrates that spring 88 has rolled up and is also slightly compressed. The characteristics of the spring 88 are chosen such that some desired amount of compression of the spring is allowed during flexion; however, the spring 88 is stiff enough such that unwanted amounts of translation of the vertebrae are resisted.

Dynamic fixation device 82 is allowed to elongate because second rod member 86 is hingedly attached to first rod member 84, thereby allowing vertical motion of second rod member 86 relative to first rod member 84. Thus, the structure of dynamic fixation device 82 provides for an articulated device that can elongate, thus accommodating the natural physiologic motion of the spine.

Dynamic fixation device 82 has application to providing segmentally applied motion control of the spine because each motion segment designated to receive an implant can have a dynamic fixation device implant customized through its dimensions and spring constant, thereby giving the patient controlled motion within a desired normal physiologic range.

In a typical use to span two vertebra, the total length of the dynamic fixation devices 10, 34, 34', 50, 58, 62, 78, and 82 may be approximately 15 to 35 mm. The geometric shape portions or hinge structures of the dynamic fixation devices, preferably occupy the central region of the implant that bridges two vertebra. That is, the geometric shapes or hinge structures occupy only a portion of the implant, thereby allowing first rod end 14 and second rod end 16 to be solid rod segments that can be interconnected to a pedicle screw using a connector device. For those devices comprising a geometric shape or hinged structure, these structures will typically occupy approximately 15 to 20 mm of the total length.

For a dynamic fixation device spanning one joint, it will expand up to approximately 5 to 10 mm in length, and will rotate forward up to between 5 to 10 degrees to accommodate flexion of the spine. Obviously, different size dynamic fixation devices may be used to accommodate the specific needs of each individual patient. More particularly, a relatively large dynamic fixation device may be needed for a large man, while a relatively small dynamic fixation device may be needed for a smaller patient, such as child or a petite woman. However, a limited number of sizes may provide adequate coverage for the majority of the patient population. For any given device, a potential elongation of the dynamic fixation device consistent with the desired flexion of the vetebral motion segment and associated distraction of the plane of the fixation device is anticipated.

Figure 11:
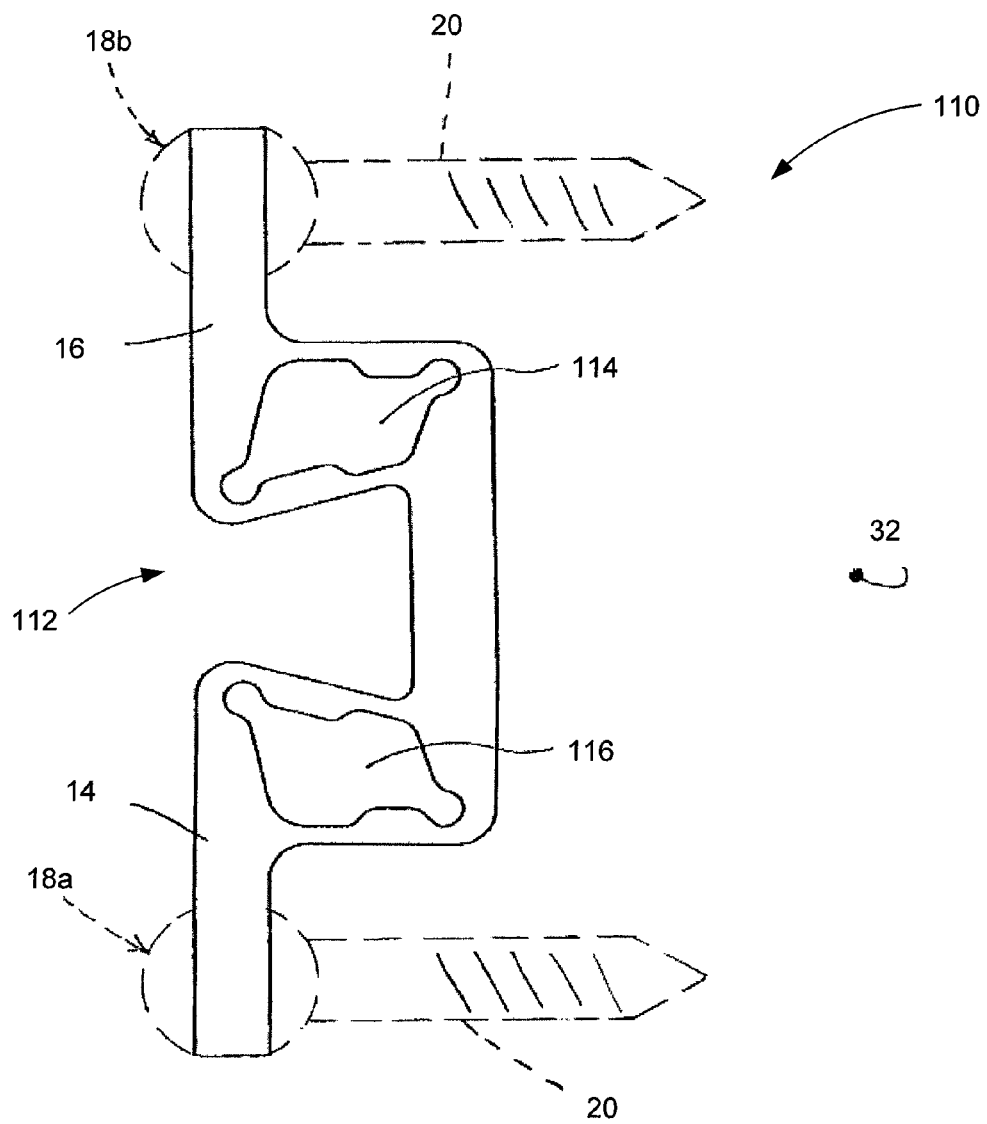
FIG. 11 is a side elevation view of a separate embodiment of a dynamic fixation device used in conjunction with pedicle screws.

Referring now to FIG. 11, yet a separate embodiment of a dynamic device 110 is shown. This embodiment includes a reverse C structure 112 that serves to provide dynamic device 110 with a mechanism that may be deflected, thereby allowing rotation and elongation of the device. Void spaces 114 and 116 in combination with the reverse C structure 112 provide structural aspects to dynamic device 110 that allow it to deflect, rotate, and elongate. This configuration creates an effective pivot point 32 that is projected anterior to the device itself, thereby allowing it to project the location of pivot toward the natural vertebra's rotation location.

Materials used to construct dynamic device 110 preferably comprise metals or metal alloys, and more preferably stainless steel or titanium. Thinned portions of the dynamic device 110 are preferably formed of titanium or stainless steel and have dimensions that allow resilient properties.

In a typical use to span two vertebra, the total length the dynamic device 110 may be approximately 25 to 30 mm, with the reverse C structure 112 occupying approximately 15 to 20 mm of the total length. The dynamic device 110 may be used to flexibly fuse a plurality of vertebra. The reverse C structure 112 may be located at specific points where bending of the spine is desired, while a rigid rod may be used at other locations desired by the physician. Where used, rigid portions may be curved, thereby influencing the implanted location of the reverse C structure 112, and thus the effective pivot point 32.

For a dynamic device 110 spanning one joint, it will expand up to approximately 5 to 10 mm in length, and will rotate up to between 5 to 10 degrees. Obviously, different size dynamic devices 110 may be used to accommodate the specific needs of each individual patient. More particularly, a relatively large dynamic device 110 may be needed for a large man, while a relatively small dynamic device 110 may be needed for a smaller patient, such as a petite woman. However, a limited number of sizes may provide adequate coverage for the majority of the patient population. For any given device, a potential elongation of the dynamic device 110 of approximately 20% is anticipated.

The reverse C structure 112 of dynamic device 110 preferably occupies the central region of the rod. That is, the reverse C structure 112 occupies only a portion of the rod, thereby allowing first end 14 and second end 16 to be solid rod segments that can be interconnected to a pedicle screws 20 using connectors 18a and 18b.

The dynamic fixation devices can be used to flexibly secure a plurality of vertebra. Alternatively, the dynamic fixation devices can be located at specific points where bending of the spine is desired, while a rigid rod may be used at other locations desired by the physician. Where used, rigid rod portions may be curved, thereby influencing the implanted location of the geometric shape hinged structures, and thus the effective pivot point.

The structures of the present invention are made from one or more materials that possesses the appropriate strength characteristics necessary to withstand loading from the human body when used in medical applications. In addition, the materials are compatible with the human body. Preferably, materials include ceramics, plastics, metals, or carbon fiber composites. More preferably, the materials are made from titanium, a titanium alloy, or stainless steel.

The above described alternative configurations offer different bending characteristics. The dimensions will vary depending upon the specific design necessary for a specific patient. More particularly, the dimensions of geometric shapes and hinged devices will likely be bigger for a large heavy man, as opposed to that needed for a small petite woman. Furthermore, the type of material used to construct the dynamic fixation devices described herein will also impact the required dimensions of the devices. Dynamic fixation devices described herein may be made of a variety of materials, preferably metals or materials demonstrating resilient characteristics, and more preferably, a titanium alloy or surgical stainless steel. Since different materials have different strength and resilient properties, the type of material used will, in part, dictate the dimensions of the rod portion required to achieve a certain function in a specific patient.

Devices disclosed herein can also be made of thermal memory materials or materials that possess different elastic properties at varying temperatures. In this aspect of the invention, the subject component(s) may be heated or cooled to a desired temperature, implanted, then subsequently allowed to cool or warm to the temperature of the ambient conditions that will exist during the usage period for the subject device, namely, normal body temperature.

It is to be understood that the present invention may have application to medical devices other than spinal implants. For example, the present invention can be used in external fixator systems.

Furthermore, it is understood that the present invention has application outside the medical field. The dynamic fixation device of the present invention is not limited to medical implants. The device could be used in seismic dampening applications. Alternatively, the present invention could be used to secure any two objects, such as in linking mechanisms, and has application to any type of mechanical device with a moving connection. Other applications, by no means exhaustive, may include connecting any articulated device, such as an implement connection to a tractor. It may also be used in heretofore static type connection applications, such as attaching an antenna to a base structure. One of skill in various of the construction arts will appreciate how to make and use the present invention in view of the guidance provided herein (with respect to a surgical application) and in view of the figures set forth herein.

While various embodiments of the present invention have been described in detail, it is apparent that modifications and adaptations of those embodiments will occur to those skilled in the art. However, it is to be expressly understood that such modifications and adaptations are within the spirit and scope of the present invention, as set forth in the following

What is claimed is:

1. A vertebral implant assembly for posterior attachment to a first vertebra and an adjacent second vertebra of a spine of a patient to allow controlled bending of the first vertebra relative to the adjacent second vertebra, comprising:
- a first pedicle screw adapted for posterior attachment to the first vertebra, and a second pedicle screw adapted for posterior attachment to the adjacent second vertebra;
- a first connector interconnectable to the first pedicle screw and a second connector interconnectable to the second pedicle screw; and
- a dynamic fixation member, comprising:
  - a first rod arm interconnectable to the first pedicle screw by the first connector, and a second rod arm interconnectable to the second pedicle screw by the second connector; and
  - a deformable portion connected to the first and second rod arms, the deformable portion including an upper member with a first void space and a lower member with a second void space, the first void space and second void space each including at least two rounded inner corners, wherein the upper member and the lower member further comprise a variable thickness, and wherein a connecting member interconnects the upper member to the lower member;
  - a gap located between a lower surface of the first rod arm and an upper surface of the second rod arm, wherein the gap extends anteriorly between the upper member and lower member to a posterior side of the connecting member, and wherein a first gap height is greater adjacent the connecting member than a second gap height located between the lower surface of the first rod arm and the upper surface of the second rod arm.

2. The vertebral implant assembly of claim 1, wherein the upper member and the lower member comprise thinned portions adjacent the connecting member.

3. The vertebral implant assembly of claim 2, wherein each of the upper and lower members comprise a top substantially anterior-posterior aligned arm and a bottom substantially anterior-posterior aligned arm bordering each void space, and wherein the top and the bottom substantially anterior-posterior aligned arms each comprise thinned portions.

4. The vertebral implant assembly of claim 2, wherein the upper member, the lower member and the connecting member substantially comprise a reverse C shape.

5. A deformable member configured to be interconnected in a posterior orientation to a first vertebra using a first pedicle screw and a first connector, and an adjacent second vertebra using a second pedicle screw and a second connector, the deformable member comprising:
- a first rod arm configured to be interconnected to the first pedicle screw using the first connector, and a second rod arm configured to be interconnected to the second pedicle screw using the second connector;
- an upper member connected to the first rod arm, the upper member including a first void space partially enclosed by an upper member top section and an upper member bottom section;
- a lower member connected to the second rod arm, the lower member including a second void space partially enclosed by a lower member top section and a lower member bottom section;
- a connecting member interconnecting the upper member to the lower member; and
- a gap located between a lower surface of the first rod arm and an upper surface of the second rod arm, wherein the gap extends between the upper member and lower member to a side of the connecting member, and wherein a first gap height is greater adjacent the connecting member than a second gap height located between the lower surface of the first rod arm and the upper surface of the second rod arm;
- wherein, when implanted posteriorly in the patient, the deformable member allows controlled bending motion while limiting sagittal translation of the first vertebra relative to the adjacent second vertebra.

6. The deformable member of claim 5, wherein the void spaces each include at least two rounded inner corners.

7. The deformable member of claim 5, wherein the upper member and the lower member comprise thinned portions adjacent the connecting member.

8. The deformable member of claim 7, wherein the upper member, the lower member and the connecting member substantially comprise a reverse C shape.

9. A deformable member for use in dynamic fixation of a first vertebra and an adjacent second vertebra, the deformable member comprising:
- a first rod arm and a second rod arm;
- an upper member connected to the first rod arm, the upper member including a first void space partially enclosed by an upper member top section and an upper member bottom section;
- a lower member connected to the second rod arm, the lower member including a second void space partially enclosed by a lower member top section and a lower member bottom section;
- a connecting member interconnecting the upper member to the lower member; and
- a gap located between a lower surface of the first rod arm and an upper surface of the second rod arm, wherein the gap extends between the upper member and lower member to a side of the connecting member, and wherein a first gap height is greater adjacent the connecting member than a second gap height located between the lower surface of the first rod arm and the upper surface of the second rod arm.

* * * * *